(12) United States Patent
Stierli et al.

(10) Patent No.: US 8,304,444 B2
(45) Date of Patent: Nov. 6, 2012

(54) PYRAZOLE CARBOXYLIC ACID AMIDES USEFUL AS MICROBIOCIDES

(75) Inventors: Daniel Stierli, Stein (CH); Harald Walter, Stein (CH); Hans Tobler, Basel (CH)

(73) Assignee: Syngenta Crop Protection, LLC, Greensboro, NC (US)

( * ) Notice: Subject to any disclaimer, the term of this patent is extended or adjusted under 35 U.S.C. 154(b) by 253 days.

(21) Appl. No.: 12/663,112

(22) PCT Filed: Jun. 6, 2008

(86) PCT No.: PCT/EP2008/004547
§ 371 (c)(1),
(2), (4) Date: Dec. 4, 2009

(87) PCT Pub. No.: WO2008/148570
PCT Pub. Date: Dec. 11, 2008

(65) Prior Publication Data
US 2010/0173966 A1    Jul. 8, 2010

(30) Foreign Application Priority Data

Jun. 8, 2007 (EP) ..................................... 07011297
Mar. 11, 2008 (EP) ..................................... 08004436

(51) Int. Cl.
*A01N 43/56* (2006.01)
*C07D 231/10* (2006.01)
*A01P 3/00* (2006.01)
(52) U.S. Cl. .................................... 514/406; 548/374.1
(58) Field of Classification Search .................. None
See application file for complete search history.

(56) References Cited

FOREIGN PATENT DOCUMENTS

EP     1787981     5/2007
EP     1792901     6/2007

*Primary Examiner* — Kamal Saeed
(74) *Attorney, Agent, or Firm* — Kody Jones

(57) ABSTRACT

Compounds of the formula (I), in which the substituents are as defined in claim 1 are suitable for use as microbiocides.

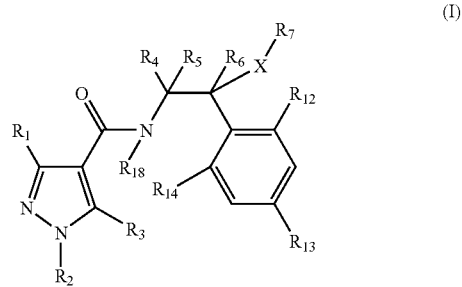

14 Claims, No Drawings

PYRAZOLE CARBOXYLIC ACID AMIDES USEFUL AS MICROBIOCIDES

This application is a 371 of International Application No. PCT/EP2008/004547 filed Jun. 6, 2008, which claims priority to EP 07011297.4 filed Jun. 8, 2007, and EP 08004436.5 filed Mar. 11, 2008, the contents of which are incorporated herein by reference.

The present invention relates to novel microbiocidally active, in particular fungicidally active, ethyl amides. It further relates to intermediates used in the preparation of these compounds, to compositions which comprise these compounds and to their use in agriculture or horticulture for controlling or preventing infestation of plants by phytopathogenic microorganisms, preferably fungi.

N-[2-(phenyl)ethyl]-carboxamide derivatives and their use as fungicides are described in EP-1787981A1 and WO 2007/060164. Pyrazole-4-carboxylic acid amide derivatives and their use as pest-controlling agents are described in JP-2001-342179. Similar compounds are also known in other fields of technology, for example, the use of pyrazole-amides and sulfonamides as pain therapeutics is described in WO 03/037274.

It has been found that novel ethyl amides have microbiocidal activity.

The present invention thus provides compounds of the formula I

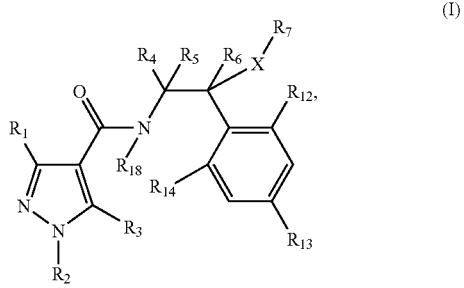

(I)

wherein
$R_1$ is halogenmethyl;
$R_2$ is $C_1$-$C_4$alkyl, $C_1$-$C_4$halogenalkyl, $C_1$-$C_4$alkoxy-$C_1$-$C_4$alkyl or $C_1$-$C_4$halogenalkoxy-$C_1$-$C_4$alkyl; and
$R_3$ is hydrogen, halogen or cyano;
$R_4$, $R_5$ and $R_6$ independently of each other stand for hydrogen, halogen, nitro, $C_1$-$C_6$alkyl, which is unsubstituted or substituted by one or more substituents $R_8$, $C_3$-$C_6$cycloalkyl, which is unsubstituted or substituted by one or more substituents $R_8$, $C_2$-$C_6$alkenyl, which is unsubstituted or substituted by one or more substituents $R_8$, $C_2$-$C_6$alkynyl, which is unsubstituted or substituted by one or more substituents $R_8$;
or $R_4$ and $R_5$ together are a $C_2$-$C_5$alkylene group, which is unsubstituted or substituted by one or more $C_1$-$C_6$alkyl groups;
X is oxygen, sulfur, —N($R_{10}$)— or —N($R_{11}$)—O—;
$R_{10}$ and $R_{11}$ independently of each other stands for hydrogen or $C_1$-$C_6$alkyl;
$R_7$ stands for $C_1$-$C_6$alkyl, which is unsubstituted or substituted by one or more substituents $R_9$, $C_3$-$C_6$cycloalkyl, which is unsubstituted or substituted by one or more substituents $R_9$, $C_2$-$C_6$alkenyl, which is unsubstituted or substituted by one or more substituents $R_9$, $C_2$-$C_6$alkynyl, which is unsubstituted or substituted by one or more substituents $R_9$;

$R_{12}$ stands for halogen, $C_1$-$C_6$haloalkoxy, $C_1$-$C_6$haloalkylthio, cyano, nitro, —C($R^a$)=N(OR$^b$), $C_1$-$C_6$alkyl, which is unsubstituted or substituted by one or more substituents $R_{15}$, $C_3$-$C_6$cycloalkyl, which is unsubstituted or substituted by one or more substituents $R_{15}$, $C_6$-$C_{14}$bicycloalkyl, which is unsubstituted or substituted by one or more substituents $R_{15}$, $C_2$-$C_6$alkenyl, which is unsubstituted or substituted by one or more substituents $R_{15}$, $C_2$-$C_6$alkynyl, which is unsubstituted or substituted by one or more substituents $R_{15}$, phenyl, which is unsubstituted or substituted by one or more substituents $R_{15}$, phenoxy, which is unsubstituted or substituted by one or more substituents $R_{15}$ or pyridinyloxy, which is unsubstituted or substituted by one or more substituents $R_{15}$;
$R_{13}$ stands for hydrogen, halogen, $C_1$-$C_6$haloalkoxy, $C_1$-$C_6$haloalkylthio, cyano, nitro, —C($R^c$)=N(OR$^d$), $C_1$-$C_6$alkyl, which is unsubstituted or substituted by one or more substituents $R_{16}$, $C_3$-$C_6$cycloalkyl, which is unsubstituted or substituted by one or more substituents $R_{16}$, $C_6$-$C_{14}$bicycloalkyl, which is unsubstituted or substituted by one or more substituents $R_{16}$, $C_2$-$C_6$alkenyl, which is unsubstituted or substituted by one or more substituents $R_{16}$, $C_2$-$C_6$alkynyl, which is unsubstituted or substituted by one or more substituents $R_{16}$, phenyl, which is unsubstituted or substituted by one or more substituents $R_{16}$, phenoxy, which is unsubstituted or substituted by one or more substituents $R_{16}$ or pyridinyloxy, which is unsubstituted or substituted by one or more substituents $R_{16}$;
$R_{14}$ stands for hydrogen, halogen, $C_1$-$C_6$haloalkoxy, $C_1$-$C_6$haloalkylthio, cyano, nitro, —C($R^e$)=N(OR$^f$), $C_1$-$C_6$alkyl, which is unsubstituted or substituted by one or more substituents $R_{17}$, $C_3$-$C_6$cycloalkyl, which is unsubstituted or substituted by one or more substituents $R_{17}$, $C_6$-$C_{14}$bicycloalkyl, which is unsubstituted or substituted by one or more substituents $R_{17}$, $C_2$-$C_6$alkenyl, which is unsubstituted or substituted by one or more substituents $R_{17}$, $C_2$-$C_6$alkynyl, which is unsubstituted or substituted by one or more substituents $R_{17}$, phenyl, which is unsubstituted or substituted by one or more substituents $R_{17}$, phenoxy, which is unsubstituted or substituted by one or more substituents $R_{17}$ or pyridinyloxy, which is unsubstituted or substituted by one or more substituents $R_{17}$;
each $R_8$, $R_9$, $R_{15}$, $R_{16}$ and $R_{17}$ is independently of each other halogen, nitro, $C_1$-$C_6$alkoxy, $C_1$-$C_6$halogenalkoxy, $C_1$-$C_6$alkylthio, $C_1$-$C_6$halogenalkylthio, $C_3$-$C_6$alkenyloxy, $C_3$-$C_6$alkynyloxy or —C($R^g$)=N(OR$^h$);
each $R^a$, $R^c$ $R^e$ and $R^g$ is independently of each other hydrogen or $C_1$-$C_6$alkyl;
each $R^b$, $R^d$ $R^f$ and $R^h$ is independently of each other $C_1$-$C_6$alkyl;
$R_{18}$ is hydrogen or $C_3$-$C_7$cycloalkyl;
and tautomers/isomers/enantiomers of these compounds.

The alkyl groups occurring in the definitions of the substituents can be straight-chain or branched and are, for example, methyl, ethyl, n-propyl, n-butyl, n-pentyl, n-hexyl, iso-propyl, n-butyl, sec-butyl, iso-butyl or tert-butyl. Alkoxy, alkenyl and alkynyl radicals are derived from the alkyl radicals mentioned. The alkenyl and alkynyl groups can be mono- or di-unsaturated.

The cycloalkyl groups occurring in the definitions of the substituents are, for example, cyclopropyl, cyclobutyl, cyclopentyl, cyclohexyl or cycloheptyl.

The bicycloalkyl groups occurring in the definitions of the substituents are, depending on the ring size, bicyclo[2.1.1]hexane, bicyclo[2.2.1]heptane, bicyclo[2.2.2]octane, bicyclo[3.2.1]octane, bicyclo[3.2.2]nonane, bicyclo[4.2.2]decane, bicyclo[4.3.2]undecane, adamantane and the like.

Halogen is generally fluorine, chlorine, bromine or iodine, preferably fluorine, bromine or chlorine. This also applies, correspondingly, to halogen in combination with other meanings, such as halogenalkyl or halogenalkoxy.

Halogenalkyl groups preferably have a chain length of from 1 to 4 carbon atoms. Halogenalkyl is, for example, fluoromethyl, difluoromethyl, trifluoromethyl, chloromethyl, dichloromethyl, trichloromethyl, 2,2,2-trifluoroethyl, 2-fluoroethyl, 2-chloroethyl, pentafluoroethyl, 1,1-difluoro-2,2,2-trichloroethyl, 2,2,3,3-tetrafluoroethyl and 2,2,2-trichloroethyl; preferably trichloromethyl, difluorochloromethyl, difluoromethyl, trifluoromethyl and dichlorofluoromethyl.

Suitable halogenalkenyl groups are alkenyl groups which are mono- or polysubstituted by halogen, halogen being fluorine, chlorine, bromine and iodine and in particular fluorine and chlorine, for example 2,2-difluoro-1-methylvinyl, 3-fluoropropenyl, 3-chloropropenyl, 3-bromopropenyl, 2,3,3-trifluoropropenyl, 2,3,3-trichloropropenyl and 4,4,4-trifluorobut-2-en-1-yl.

Suitable halogenalkynyl groups are, for example, alkynyl groups which are mono- or polysubstituted by halogen, halogen being bromine, iodine and in particular fluorine and chlorine, for example 3-fluoropropynyl, 3-chloropropynyl, 3-bromopropynyl, 3,3,3-trifluoropropynyl and 4,4,4-trifluorobut-2-yn-1-yl.

Alkoxy is, for example, methoxy, ethoxy, propoxy, i-propoxy, n-butoxy, isobutoxy, sec-butoxy and tert-butoxy; preferably methoxy and ethoxy. Halogenalkoxy is, for example, fluoromethoxy, difluoromethoxy, trifluoromethoxy, 2,2,2-trifluoroethoxy, 1,1,2,2-tetrafluoroethoxy, 2-fluoroethoxy, 2-chloroethoxy, 2,2-difluoroethoxy and 2,2,2-trichloroethoxy; preferably difluoromethoxy, 2-chloroethoxy and trifluoromethoxy. Alkylthio is, for example, methylthio, ethylthio, propylthio, isopropylthio, n-butylthio, isobutylthio, sec-butylthio or tert-butylthio, preferably methylthio and ethylthio.

Alkoxyalkyl is, for example, methoxymethyl, methoxyethyl, ethoxymethyl, ethoxyethyl, n-propoxymethyl, n-propoxyethyl, isopropoxymethyl or isopropoxyethyl.

In the context of the present invention "substituted by one or more substituents" in the definition of substituents $R_4$, $R_5$, $R_6$, $R_7$, $R_{12}$, $R_{13}$ and $R_{14}$, means typically, depending on the chemical structure of substituents $R_4$, $R_5$, $R_6$, $R_7$, $R_{12}$, $R_{13}$ and $R_{14}$, monosubstituted to nine-times substituted, preferably monosubstituted to five-times substituted, more preferably mono-, double- or triple-substituted.

The compounds of the formula I, wherein $R_{18}$ is hydrogen, may occur in different tautomeric forms. For example, compounds of formula I exist in the tautomeric forms $I_I$ and $I_{II}$:

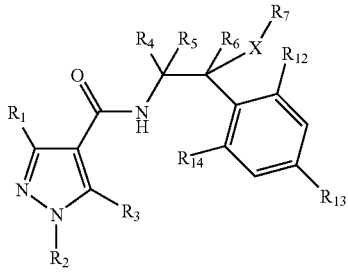

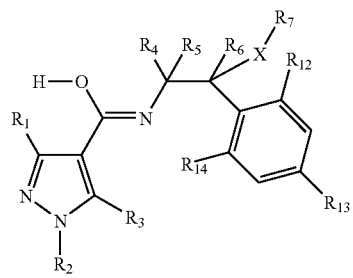

The invention covers all those tautomeric forms and mixtures thereof.

Preferably $R_{18}$ is hydrogen. In further preferred compounds of formula I, $R_1$ is $CF_3$, $CF_2H$ or $CFH_2$, preferably $CF_2H$ or $CF_3$, more preferably $CF_2H$; $R_2$ is $C_1$-$C_4$alkyl, preferably methyl; and $R_3$ is hydrogen or halogen, preferably hydrogen. In one embodiment of the invention, $R_1$ is $CF_2H$; $R_2$ is methyl and $R_3$ is hydrogen.

In preferred compounds of formula I, $R_4$ is selected from hydrogen, halogen, nitro, $C_1$-$C_6$alkyl, which is unsubstituted or substituted by one or more substituents $R_8$, $C_3$-$C_6$cycloalkyl, which is unsubstituted or substituted by one or more substituents $R_8$, $C_2$-$C_6$alkenyl, which is unsubstituted or substituted by one or more substituents $R_8$, $C_2$-$C_6$alkynyl, which is unsubstituted or substituted by one or more substituents $R_8$.

In further preferred compounds of formula I, $R_4$ is hydrogen or $C_1$-$C_6$alkyl, which is unsubstituted or substituted by one or more substituents $R_8$.

In further preferred compounds of formula I, $R_4$ is hydrogen, $C_1$-$C_6$alkyl or $C_1$-$C_6$haloalkyl.

In further preferred compounds of formula I, $R_4$ is hydrogen or $C_1$-$C_6$alkyl.

In further preferred compounds of formula I, $R_4$ is hydrogen or methyl.

In further preferred compounds of formula I, $R_4$ is hydrogen.

In further preferred compounds of formula I, $R_4$ is methyl.

In further preferred compounds of formula I, $R_4$ is selected from halogen, nitro, $C_1$-$C_6$alkyl, which is unsubstituted or substituted by one or more substituents $R_8$, $C_3$-$C_6$cycloalkyl, which is unsubstituted or substituted by one or more substituents $R_8$, $C_2$-$C_6$alkenyl, which is unsubstituted or substituted by one or more substituents $R_8$, $C_2$-$C_6$alkynyl, which is unsubstituted or substituted by one or more substituents $R_8$.

In further preferred compounds of formula I, $R_4$ is $C_1$-$C_6$alkyl, which is unsubstituted or substituted by one or more substituents $R_8$.

In further preferred compounds of formula I, $R_4$ is $C_1$-$C_6$alkyl or $C_1$-$C_6$haloalkyl.

In further preferred compounds of formula I, $R_4$ is $C_1$-$C_6$alkyl.

In further preferred compounds of formula I, $R_4$ is $C_1$-$C_6$haloalkyl, preferably $CF_3$, $CF_2H$ or $CH_2F$.

In preferred compounds of formula I, $R_5$ and $R_6$ independently of each other stand for hydrogen, halogen, nitro, $C_1$-$C_6$alkyl, which is unsubstituted or substituted by one or more substituents $R_8$, $C_3$-$C_6$cycloalkyl, which is unsubstituted or substituted by one or more substituents $R_8$, $C_2$-$C_6$alkenyl, which is unsubstituted or substituted by one or more substituents $R_8$, $C_2$-$C_6$alkynyl, which is unsubstituted or substituted by one or more substituents $R_8$.

In further preferred compounds of formula I, $R_5$ and $R_6$ independently of each other stand for hydrogen or $C_1$-$C_6$alkyl.

In further preferred compounds of formula I, $R_5$ and $R_6$ are both hydrogen.

In preferred compounds of formula I, $R_8$ stands for halogen, $C_1$-$C_6$alkoxy, $C_1$-$C_6$halogenalkoxy, $C_1$-$C_6$alkylthio or $C_1$-$C_6$halogenalkylthio.

In further preferred compounds of formula I, $R_8$ stands for halogen or $C_1$-$C_6$alkoxy.

In preferred compounds of formula I, X is oxygen.

In further preferred compounds of formula I, X is sulfur.

In further preferred compounds of formula I, X is —N($R_{10}$)—.

In further preferred compounds of formula I, X is —N($R_{11}$)—O—.

In preferred compounds $R_{10}$ is hydrogen or methyl.

In preferred compounds $R_{11}$ is hydrogen or methyl. In one embodiment of the invention $R_{11}$ is hydrogen.

In preferred compounds of formula I, $R_7$ stands for $C_1$-$C_6$alkyl, which is unsubstituted or substituted by one or more substituents $R_9$, $C_2$-$C_6$alkenyl, which is unsubstituted or substituted by one or more substituents $R_9$ or $C_2$-$C_6$alkynyl, which is unsubstituted or substituted by one or more substituents $R_9$.

In further preferred compounds of formula I, $R_7$ stands for $C_1$-$C_6$alkyl, $C_2$-$C_6$alkenyl or $C_2$-$C_6$alkynyl.

In further preferred compounds of formula I, $R_7$ stands for $C_1$-$C_6$alkyl, preferably methyl.

In preferred compounds of formula I, $R_9$ stands for halogen, $C_1$-$C_6$alkoxy, $C_1$-$C_6$halogenalkoxy $C_1$-$C_6$alkylthio or $C_1$-$C_6$halogenalkylthio.

In further preferred compounds of formula I, $R_9$ stands for halogen or $C_1$-$C_6$alkoxy.

In preferred compounds
$R_{12}$ stands for halogen, $C_1$-$C_6$haloalkoxy, $C_1$-$C_6$haloalkylthio, cyano, nitro, —C($R^a$)=N(O$R^b$), $C_1$-$C_6$alkyl, which is unsubstituted or substituted by one or more substituents $R_{15}$, $C_3$-$C_6$cycloalkyl, which is unsubstituted or substituted by one or more substituents $R_{15}$, $C_6$-$C_{14}$bicycloalkyl, which is unsubstituted or substituted by one or more substituents $R_{15}$, $C_2$-$C_6$alkenyl, which is unsubstituted or substituted by one or more substituents $R_{15}$, $C_2$-$C_6$alkynyl, which is unsubstituted or substituted by one or more substituents $R_{15}$, phenyl, which is unsubstituted or substituted by one or more substituents $R_{15}$, phenoxy, which is unsubstituted or substituted by one or more substituents $R_{15}$ or pyridinyloxy, which is unsubstituted or substituted by one or more substituents $R_{15}$;
$R_{13}$ stands for halogen, $C_1$-$C_6$haloalkoxy, $C_1$-$C_6$haloalkylthio, cyano, nitro, —C($R^c$)=N(O$R^d$), $C_1$-$C_6$alkyl, which is unsubstituted or substituted by one or more substituents $R_{16}$, $C_3$-$C_6$cycloalkyl, which is unsubstituted or substituted by one or more substituents $R_{16}$, $C_6$-$C_{14}$bicycloalkyl, which is unsubstituted or substituted by one or more substituents $R_{16}$, $C_2$-$C_6$alkenyl, which is unsubstituted or substituted by one or more substituents $R_{16}$, $C_2$-$C_6$alkynyl, which is unsubstituted or substituted by one or more substituents $R_{16}$, phenyl, which is unsubstituted or substituted by one or more substituents $R_{16}$, phenoxy, which is unsubstituted or substituted by one or more substituents $R_{16}$ or pyridinyloxy, which is unsubstituted or substituted by one or more substituents $R_{16}$; and
$R_{14}$ stands for hydrogen, halogen, $C_1$-$C_6$haloalkoxy, $C_1$-$C_6$haloalkylthio, cyano, nitro, —C($R^e$)=N(O$R^f$), $C_1$-$C_6$alkyl, which is unsubstituted or substituted by one or more substituents $R_{17}$, $C_3$-$C_6$cycloalkyl, which is unsubstituted or substituted by one or more substituents $R_{17}$, $C_6$-$C_{14}$bicycloalkyl, which is unsubstituted or substituted by one or more substituents $R_{17}$, $C_2$-$C_6$alkenyl, which is unsubstituted or substituted by one or more substituents $R_{17}$, $C_2$-$C_6$alkynyl, which is unsubstituted or substituted by one or more substituents $R_{17}$, phenyl, which is unsubstituted or substituted by one or more substituents $R_{17}$, phenoxy, which is unsubstituted or substituted by one or more substituents $R_{17}$ or pyridinyloxy, which is unsubstituted or substituted by one or more substituents $R_{17}$.

In preferred compounds
$R_{12}$ and $R_{13}$ independently of one another are halogen, cyano, $C_1$-$C_6$alkyl, $C_2$-$C_6$alkynyl, $C_1$-$C_6$alkoxy, $C_1$-$C_6$halogenalkyl, $C_1$-$C_6$halogenalkoxy, —C(H)=N(O—$C_1$-$C_6$alkyl) or phenyl, which is unsubstituted or substituted by one or more halogens; and $R_{14}$ is hydrogen, halogen, cyano, $C_1$-$C_6$alkyl, $C_2$-$C_6$alkynyl, $C_1$-$C_6$alkoxy, $C_1$-$C_6$halogenalkyl, $C_1$-$C_6$halogenalkoxy, —C(H)=N(O—$C_1$-$C_6$alkyl) or phenyl, which is unsubstituted or substituted by one or more halogens.

In further preferred compounds
$R_{12}$ and $R_{13}$ independently of one another are halogen, cyano, $C_2$-$C_6$alkynyl, $C_1$-$C_6$halogenalkyl, $C_1$-$C_6$halogenalkoxy, —C(H)=N(O—$C_1$-$C_6$alkyl) or phenyl, which is substituted halogen; and $R_{14}$ is hydrogen, halogen, cyano, $C_2$-$C_6$alkynyl, $C_1$-$C_6$halogenalkyl, $C_1$-$C_6$halogenalkoxy, —C(H)=N(O—$C_1$-$C_6$alkyl) or phenyl, which is substituted halogen.

In further preferred compounds
$R_{12}$ and $R_{13}$ independently of one another are halogen, $C_2$-$C_6$alkynyl, $C_1$-$C_6$halogenalkyl or —C(H)=N(O—$C_1$-$C_6$alkyl); and $R_{14}$ is hydrogen, halogen, $C_2$-$C_6$alkynyl, $C_1$-$C_6$halogenalkyl or —C(H)=N(O—$C_1$-$C_6$alkyl).

In further preferred compounds
$R_{12}$ and $R_{13}$ independently of one another are halogen or $C_1$-$C_6$halogenalkyl; and $R_{14}$ is hydrogen, halogen or $C_1$-$C_6$halogenalkyl.

In further preferred compounds
$R_{12}$ and $R_{13}$ independently of one another are halogen or $C_1$-$C_6$halogenalkyl, preferably halogen; and $R_{14}$ is hydrogen.

In further preferred compounds
$R_{12}$, $R_{13}$ and $R_{14}$ independently of one another are halogen or $C_1$-$C_6$halogenalkyl, preferably halogen.

Compounds of formula I may be prepared by reacting a compound of formula II

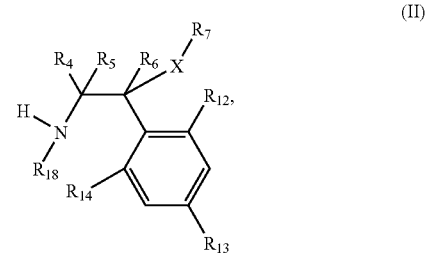

(II)

in which $R_4$, $R_5$, $R_6$, $R_7$, X, $R_{12}$, $R_{13}$ and $R_{14}$ are as defined under formula I; with a compound of formula III

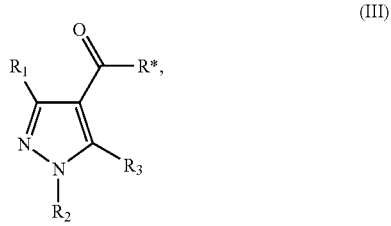

(III)

in which $R_1$, $R_2$ and $R_3$ are as defined under formula I, and R* is halogen, hydroxy or $C_{1-6}$ alkoxy, preferably chloro, in the presence of a base, such as triethylamine, Hunig base, sodium bicarbonate, sodium carbonate, potassium carbonate, pyridine or quinoline, but preferably triethylamine, and in a solvent, such as diethylether, TBME, THF, dichloromethane, chloroform, DMF or NMP, for between 10 minutes and 48 hours, preferably 12 to 24 hours, and between 0° C. and reflux, preferably 20 to 25° C.

When R* is hydroxy, a coupling agent, such as benzotriazol-1-yloxytris(dimethylamino) phosphoniumhexafluorophosphate, bis-(2-oxo-3-oxazolidinyl)-phosphinic acid chloride (BOP—CI), N,N'-dicyclohexylcarbodiimide (DCC) or 1,1'-carbonyl-diimidazole (CDI), may be used.

The intermediates of the formula II

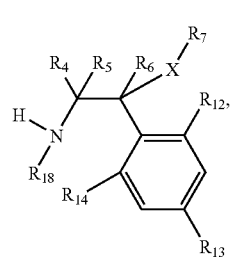

(II)

in which $R_4$, $R_5$, $R_6$, $R_7$, X, $R_{12}$, $R_{13}$, $R_{14}$ and $R_{18}$ are as defined under formula I, preferably wherein $R_{18}$ is hydrogen; are novel and were developed specifically for the preparation of the compounds of the formula I. Accordingly, these intermediates of the formula II also form part of the subject-matter of the present invention.

Intermediates of Formula IIa

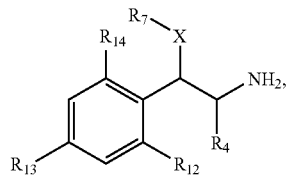

(IIA)

Scheme 2:

wherein $R_4$, X, $R_7$, $R_{12}$, $R_{13}$ and $R_{14}$ are as defined under formula I may be prepared as described in reaction scheme 1.

Scheme 1:

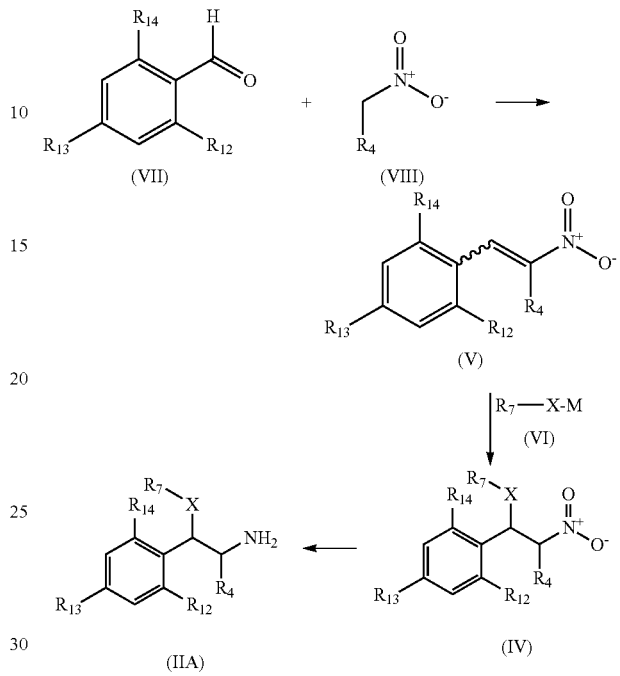

Intermediates of Formula IIb

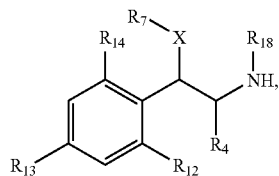

(IIB)

wherein $R_4$, X, $R_7$, $R_{12}$, $R_{13}$ and $R_{14}$ are as defined under formula II and $R_{18}$ is $C_3$-$C_7$cycloalkyl, may be prepared as described in reaction scheme 2:

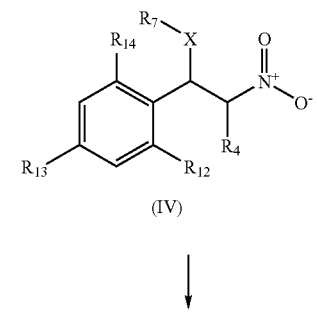

(IV)

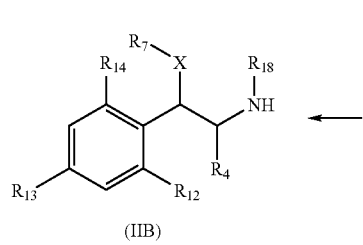

(IIB)

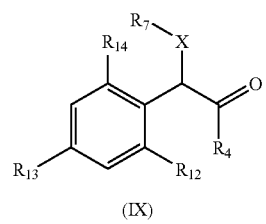

(IX)

α-alkoxyketones IX, in which $R_4$, $R_7$, $R_{12}$, $R_{13}$ and $R_{14}$ are as defined under formula I, can be prepared by the Nef reaction of a nitroalkoxyalkanes IV, in which $R_4$, $R_7$, $R_{12}$, $R_{13}$ and $R_{14}$ are as defined under formula I, under either acidic or basic conditions. See for example: W. E Noland, Chem. Rev. 55, 137 (1955); G. A. Olah, Synthesis, 44 (1980); K. Stelion, M. A Poupart, J. Org. Chem., 50, 4971 (1985); G. W. Kabalka, Synthesis, 654 (1985); P. S. Vankar, R. Rathore, Synth. Commun. 17, 195 (1987) and references cited. Another method for the oxidative cleavage of the nitronate anion under mild conditions via trialkylsilyl nitronates upon treatment with MCPA is described by J. M. Aizpurua, M. Oiarbide and C. Palomo in THL, Vol. 28, No. 44, 5361-5364 (1987).

Amines of formula IIB wherein $R_4$, X, $R_7$, $R_{12}$, $R_{13}$, $R_{14}$ are as defined under formula II and $R_{18}$ is $C_3$-$C_7$cycloalkyl may be prepared according to a process which comprises the reaction of a compound of general formula IX with an cycloalkylamine of formula X to provide an imine derivative of general formula XI. A second step comprises the reduction of the imine derivative of general formula XI by hydrogenation or by an hydride donor, in the same or a different pot to provide an amine of general formula IIB or one of its salt. Preferably, the hydride donor is chosen as being metal or metal hydride such as $LiAlH_4$, $NaBH_4$, $NaBH_3CN$, $NaBH(OAc)_3$, $KBH_4$, $B_2H_6$.

Nitroalkenes of formula V, in which $R_4$, $R_{12}$, $R_{13}$ and $R_{14}$ are as defined under formula I, can be prepared by the reaction of a carbonyl compound of formula VII, in which $R_{12}$, $R_{13}$ and $R_{14}$ are as defined under formula I, with a nitroalkane of formula VIII, in which $R_4$ is as defined under formula I, in the presence of acetic acid and ammonium acetate at temperatures between ambient temperature and reflux temperature.

Michael addition of a compound of formula VI, in which $R_7$ and X are as defined under formula I and M is Li, Na, K or hydrogen, to the nitroalkenes of formula V may be accomplished using earth alkali alcoholates preferred sodium, potassium and lithium salts in the corresponding alcohol, toluene or an ether solvent such as diethyl ether, ethylene glycol dimethyl ether, diethylene glycol dimethyl ether, tetrahydrofuran or dioxane to form the nitroalkoxyalkanes VI, in which $R_4$, $R_7$, $R_{12}$, $R_{13}$ and $R_{14}$ are as defined under formula I. Reduction of the nitroalkoxyalkanes of the formula IV to form the intermediates of formula IIA may be accomplished using zinc in an alcohol solvent such as methanol, ethanol or isopropanol and an aqueous acid such as hydrochloric acid sulphuric acid, or more preferred (see example P2c2) by catalytic reduction over Raney nickel or a noble metal catalyst. The reduction is carried out at temperatures of between 20-80° C.

The other intermediates of the formula II may be prepared according to reaction scheme 1 or 2 or in analogy to this reaction scheme.

For preparing all further compounds of the formula I functionalized according to the definitions of $R_1$, $R_2$, $R_3$, $R_4$, $R_5$, $R_6$, $R_7$, $R_{12}$, $R_{13}$, $R_{14}$, $R_{18}$ and X there are a large number of suitable known standard methods, such as alkylation, halogenation, acylation, amidation, oximation, oxidation and reduction. The choice of the preparation methods which are suitable are depending on the properties (reactivity) of the substituents in the intermediates.

The compounds of the formula III are known and some of them are commercially available. They can be prepared analogously as described, for example, in WO 00/09482, WO 02/38542, WO 04/018438, EP-O-589-301, WO 93/11117 and Arch. Pharm. Res. 2000, 23(4), 315-323.

The compounds of formula VI, VII and VIII are known and are commercially available or can be prepared according to the above-mentioned references or according to methods known in the art.

The reactions leading to compounds of the formula I are advantageously carried out in aprotic inert organic solvents. Such solvents are hydrocarbons such as benzene, toluene, xylene or cyclohexane, chlorinated hydrocarbons such as dichloromethane, trichloromethane, tetrachloromethane or chlorobenzene, ethers such as diethyl ether, ethylene glycol dimethyl ether, diethylene glycol dimethyl ether, tetrahydrofuran or dioxane, nitriles such as acetonitrile or propionitrile, amides such as N,N-dimethylformamide, diethylformamide or N-methylpyrrolidinone. The reaction temperatures are advantageously between −20° C. and +120° C. In general, the reactions are slightly exothermic and, as a rule, they can be carried out at ambient temperature. To shorten the reaction time, or else to start the reaction, the mixture may be heated briefly to the boiling point of the reaction mixture. The reaction times can also be shortened by adding a few drops of base as reaction catalyst. Suitable bases are, in particular, tertiary amines such as trimethylamine, triethylamine, quinuclidine, 1,4-diazabicyclo[2.2.2]octane, 1,5-diazabicyclo[4.3.0]non-5-ene or 1,5-diazabicyclo[5.4.0]undec-7-ene. However, inorganic bases such as hydrides, e.g. sodium hydride or calcium hydride, hydroxides, e.g. sodium hydroxide or potassium hydroxide, carbonates such as sodium carbonate and potassium carbonate, or hydrogen carbonates such as potassium hydrogen carbonate and sodium hydrogen carbonate may also be used as bases. The bases can be used as such or else with catalytic amounts of a phase-transfer catalyst, for example a crown ether, in particular 18-crown-6, or a tetraalkylammonium salt.

The compounds of formula I can be isolated in the customary manner by concentrating and/or by evaporating the solvent and purified by recrystallization or trituration of the solid residue in solvents in which they are not readily soluble, such as ethers, aromatic hydrocarbons or chlorinated hydrocarbons.

The compounds of formula I and, where appropriate, the tautomers thereof, can be present in the form of one of the isomers which are possible or as a mixture of these, for example in the form of pure isomers, such as antipodes and/or diastereomers, or as isomer mixtures, such as enantiomer mixtures, for example racemates, diastereomer mixtures or racemate mixtures, depending on the number, absolute and relative configuration of asymmetric carbon atoms which occur in the molecule and/or depending on the configuration of non-aromatic double bonds which occur in the molecule; the invention relates to the pure isomers and also to all isomer mixtures which are possible and is to be understood in each case in this sense hereinabove and hereinbelow, even when stereochemical details are not mentioned specifically in each case.

The compounds of formula I and, where appropriate, the tautomers thereof, can, if appropriate, also be obtained in the form of hydrates and/or include other solvents, for example those which may have been used for the crystallization of compounds which are present in solid form.

It has now been found that the compounds of formula I according to the invention have, for practical purposes, a very advantageous spectrum of activities for protecting useful plants against diseases that are caused by phytopathogenic microorganisms, such as fungi, bacteria or viruses.

The invention relates to a method of controlling or preventing infestation of useful plants by phytopathogenic microorganisms, wherein a compound of formula I is applied as active ingredient to the plants, to parts thereof or the locus thereof. The compounds of formula I according to the invention are distinguished by excellent activity at low rates of application, by being well tolerated by plants and by being environmentally safe. They have very useful curative, preventive and systemic properties and are used for protecting numerous useful plants. The compounds of formula I can be used to inhibit or destroy the diseases that occur on plants or parts of plants (fruit, blossoms, leaves, stems, tubers, roots) of different crops of useful plants, while at the same time protecting also those parts of the plants that grow later e.g. from phytopathogenic microorganisms.

It is also possible to use compounds of formula I as dressing agents for the treatment of plant propagation material, in particular of seeds (fruit, tubers, grains) and plant cuttings (e.g. rice), for the protection against fungal infections as well as against phytopathogenic fungi occurring in the soil.

Furthermore the compounds of formula I according to the invention may be used for controlling fungi in related areas, for example in the protection of technical materials, including wood and wood related technical products, in food storage or in hygiene management.

The compounds of formula I are, for example, effective against the phytopathogenic fungi of the following classes: Fungi imperfecti (e.g. *Botrytis, Pyricularia, Helminthosporium, Fusarium, Septoria, Cercospora and Alternaria*) and Basidiomycetes (e.g. *Rhizoctonia, Hemileia, Puccinia*). Additionally, they are also effective against the Ascomycetes classes (e.g. *Venturia and Erysiphe, Podosphaera, Monilinia, Uncinula*) and of the Oomycetes classes (e.g. *Phytophthora, Pythium, Plasmopara*). Outstanding activity has been observed against powdery mildew diseases (e.g. *Uncinula necator*). Furthermore, the novel compounds of formula I are effective against phytopathogenic bacteria and viruses (e.g. against *Xanthomonas* spp, *Pseudomonas* spp, *Erwinia amylovora* as well as against the tobacco mosaic virus). Good activity has been observed against Asian soybean rust (*Phakopsora pachyrhizi*).

Within the scope of the invention, useful plants to be protected typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, *cinnamomum*, camphor) or plants such as tobacco, nuts, coffee, eggplants, sugar cane, tea, pepper, vines, hops, bananas and natural rubber plants, as well as ornamentals.

The term "useful plants" is to be understood as including also useful plants that have been rendered tolerant to herbicides like bromoxynil or classes of herbicides (such as, for example, HPPD inhibitors, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors or PPO (protoporphyrinogen-oxidase) inhibitors) as a result of conventional methods of breeding or genetic engineering. An example of a crop that has been rendered tolerant to imidazolinones, e.g. imazamox, by conventional methods of breeding (mutagenesis) is Clearfield® summer rape (Canola). Examples of crops that have been rendered tolerant to herbicides or classes of herbicides by genetic engineering methods include glyphosate- and glufosinate-resistant maize varieties commercially available under the trade names RoundupReady®, Herculex I® and LibertyLink®.

The term "useful plants" is to be understood as including also useful plants which have been so transformed by the use of recombinant DNA techniques that they are capable of synthesising one or more selectively acting toxins, such as are known, for example, from toxin-producing bacteria, especially those of the genus *Bacillus*.

Examples of such plants are: YieldGard® (maize variety that expresses a CryIA(b) toxin); YieldGard Rootworm® (maize variety that expresses a CryIIIB(b1) toxin); YieldGard Plus® (maize variety that expresses a CryIA(b) and a CryIIIB (b1) toxin); Starlink® (maize variety that expresses a Cry9(c) toxin); Herculex I® (maize variety that expresses a CryIF(a2) toxin and the enzyme phosphinothricine N-acetyltransferase (PAT) to achieve tolerance to the herbicide glufosinate ammonium); NuCOTN 33B® (cotton variety that expresses a CryIA(c) toxin); Bollgard I® (cotton variety that expresses a CryIA(c) toxin); Bollgard II® (cotton variety that expresses a CryIA(c) and a CryIIA(b) toxin); VIPCOT® (cotton variety that expresses a VIP toxin); NewLeaf® (potato variety that expresses a CryIIIA toxin); NatureGard® Agrisure® GT Advantage (GA21 glyphosate-tolerant trait), Agrisure® CB Advantage (Bt11 corn borer (CB) trait), Agrisure® RW (corn rootworm trait) and Protecta®.

The term "useful plants" is to be understood as including also useful plants which have been so transformed by the use of recombinant DNA techniques that they are capable of synthesising antipathogenic substances having a selective action, such as, for example, the so-called "pathogenesis-related proteins" (PRPs, see e.g. EP-A-0 392 225). Examples of such antipathogenic substances and transgenic plants capable of synthesising such antipathogenic substances are known, for example, from EP-A-0 392 225, WO 95/33818, and EP-A-0 353 191. The methods of producing such transgenic plants are generally known to the person skilled in the art and are described, for example, in the publications mentioned above.

The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing.

The term "plant propagation material" is understood to denote generative parts of the plant, such as seeds, which can be used for the multiplication of the latter, and vegetative material, such as cuttings or tubers, for example potatoes. There may be mentioned for example seeds (in the strict sense), roots, fruits, tubers, bulbs, rhizomes and parts of plants. Germinated plants and young plants which are to be transplanted after germination or after emergence from the soil, may also be mentioned. These young plants may be protected before transplantation by a total or partial treatment by immersion. Preferably "plant propagation material" is understood to denote seeds.

The compounds of formula I can be used in unmodified form or, preferably, together with carriers and adjuvants conventionally employed in the art of formulation.

Therefore the invention also relates to compositions for controlling and protecting against phytopathogenic microorganisms, comprising a compound of formula I and an inert carrier, and to a method of controlling or preventing infestation of useful plants by phytopathogenic microorganisms, wherein a composition, comprising a compound of formula I as active ingredient and an inert carrier, is applied to the plants, to parts thereof or the locus thereof.

To this end compounds of formula I and inert carriers are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomising, dusting, scattering, coating or pouring, are chosen in accordance with the intended objectives and the prevailing circumstances. The compositions may also contain further adjuvants such as stabilizers, antifoams, viscosity regulators, binders or tackifiers as well as fertilizers, micronutrient donors or other formulations for obtaining special effects.

Suitable carriers and adjuvants can be solid or liquid and are substances useful in formulation technology, e.g. natural or regenerated mineral substances, solvents, dispersants, wetting agents, tackifiers, thickeners, binders or fertilizers. Such carriers are for example described in WO 97/33890.

The compounds of formula I or compositions, comprising a compound of formula I as active ingredient and an inert carrier, can be applied to the locus of the plant or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides or mixtures of several of these preparations, if desired together with further carriers, surfactants or application promoting adjuvants customarily employed in the art of formulation.

A preferred method of applying a compound of formula I, or a composition, comprising a compound of formula I as active ingredient and an inert carrier, is foliar application. The frequency of application and the rate of application will depend on the risk of infestation by the corresponding pathogen. However, the compounds of formula I can also penetrate the plant through the roots via the soil (systemic action) by drenching the locus of the plant with a liquid formulation, or by applying the compounds in solid form to the soil, e.g. in granular form (soil application). In crops of water rice such granulates can be applied to the flooded rice field. The compounds of formula I may also be applied to seeds (coating) by impregnating the seeds or tubers either with a liquid formulation of the fungicide or coating them with a solid formulation.

A formulation, i.e. a composition comprising the compound of formula I and, if desired, a solid or liquid adjuvant, is prepared in a known manner, typically by intimately mixing and/or grinding the compound with extenders, for example solvents, solid carriers and, optionally, surface-active compounds (surfactants).

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient rates of application are from 10 mg to 1 g of active substance per kg of seeds. The rate of application for the desired action can be determined by experiments. It depends for example on the type of action, the developmental stage of the useful plant, and on the application (location, timing, application method) and can, owing to these parameters, vary within wide limits.

Surprisingly, it has now been found that the compounds of formula I can also be used in methods of protecting crops of useful plants against attack by phytopathogenic organisms as well as the treatment of crops of useful plants infested by phytopathogenic organisms comprising administering a combination of glyphosate and at least one compound of formula I to the plant or locus thereof, wherein the plant is resistant or sensitive to glyphosate.

Said methods may provide unexpectedly improved control of diseases compared to using the compounds of formula I in the absence of glyphosate. Said methods may be effective at enhancing the control of disease by compounds of formula I. While the mixture of glyphosate and at least one compound of formula I may increase the disease spectrum controlled, at least in part, by the compound of formula I, an increase in the activity of the compound of formula I on disease species already known to be controlled to some degree by the compound of formula I can also be the effect observed.

Said methods are particularly effective against the phytopathogenic organisms of the kingdom Fungi, phylum Basidiomycot, class Uredinomycetes, subclass Urediniomycetidae and the order Uredinales (commonly referred to as rusts). Species of rusts having a particularly large impact on agriculture include those of the family Phakopsoraceae, particularly those of the genus *Phakopsora*, for example *Phakopsora pachyrhizi*, which is also referred to as Asian soybean rust, and those of the family Pucciniaceae, particularly those of the genus *Puccinia* such as *Puccinia graminis*, also known as stem rust or black rust, which is a problem disease in cereal crops and *Puccinia recondita*, also known as brown rust.

An embodiment of said method is a method of protecting crops of useful plants against attack by a phytopathogenic organism and/or the treatment of crops of useful plants infested by a phytopathogenic organism, said method comprising simultaneously applying glyphosate, including salts or esters thereof, and at least one compound of formula I, which has activity against the phytopathogenic organism to at least one member selected from the group consisting of the plant, a part of the plant and the locus of the plant.

Surprisingly, it has now been found that the compounds of formula I, or a pharmaceutical salt thereof, described above have also an advantageous spectrum of activity for the treatment and/or prevention of microbial infection in an animal.

"Animal" can be any animal, for example, insect, mammal, reptile, fish, amphibian, preferably mammal, most preferably human. "Treatment" means the use on an animal which has microbial infection in order to reduce or slow or stop the increase or spread of the infection, or to reduce the infection or to cure the infection. "Prevention" means the use on an animal which has no apparent signs of microbial infection in order to prevent any future infection, or to reduce or slow the increase or spread of any future infection.

According to the present invention there is provided the use of a compound of formula I in the manufacture of a medicament for use in the treatment and/or prevention of microbial infection in an animal. There is also provided the use of a compound of formula I as a pharmaceutical agent. There is also provided the use of a compound of formula I as an antimicrobial agent in the treatment of an animal. According to the present invention there is also provided a pharmaceutical composition comprising as an active ingredient a compound of formula I, or a pharmaceutically acceptable salt thereof, and a pharmaceutically acceptable diluent or carrier. This composition can be used for the treatment and/or prevention of antimicrobial infection in an animal. This pharmaceutical composition can be in a form suitable for oral administration, such as tablet, lozenges, hard capsules, aqueous suspensions, oily suspensions, emulsions dispersible powders, dispersible granules, syrups and elixirs. Alternatively this pharmaceutical composition can be in a form suitable for topical application, such as a spray, a cream or lotion. Alternatively this pharmaceutical composition can be in a form suitable for parenteral administration, for example injection. Alternatively this pharmaceutical composition can be in inhalable form, such as an aerosol spray.

The compounds of formula I are effective against various microbial species able to cause a microbial infection in an animal. Examples of such microbial species are those causing Aspergillosis such as *Aspergillus fumigatus, A. flavus, A. terrus, A. nidulans* and *A. niger*, those causing Blastomycosis such as *Blastomyces dermatitidis*; those causing Candidiasis such as *Candida albicans, C. glabrata, C. tropicalis, C. parapsilosis, C. krusei* and *C. lusitaniae*; those causing Coccidioidomycosis such as *Coccidioides immitis*; those causing Cryptococcosis such as *Cryptococcus neoformans*; those causing Histoplasmosis such as *Histoplasma capsulatum* and those causing Zygomycosis such as *Absidia corymbifera, Rhizomucor pusillus* and *Rhizopus arrhizus*. Further examples are *Fusarium* Spp such as *Fusarium oxysporum* and *Fusarium solani* and *Scedosporium* Spp such as *Scedosporium apiospermum* and *Scedosporium prolificans*. Still further examples are *Microsporum* Spp, *Trichophyton* Spp, *Epidermophyton* Spp, *Mucor* Spp, *Sporothorix* Spp, *Phialophora* Spp, *Cladosporium* Spp, *Petriellidium* spp, *Paracoccidioides* Spp and *Histoplasma* Spp.

The following non-limiting Examples illustrate the above-described invention in greater detail without limiting it.

PREPARATION EXAMPLES

Example P1

Preparation of 3-difluoromethyl-1-methyl-1H-pyrazole-4-carboxylic acid [2-(2,4-dichlorophenyl)-2-methoxy-1-methyl-ethyl]-amide
(Compound No. 1.14)

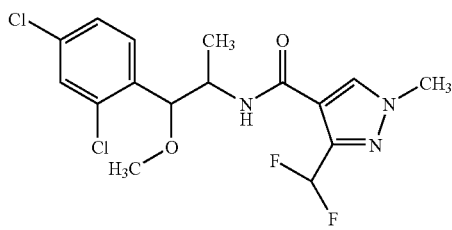

a) Preparation of 3-difluoromethyl-1-methyl-1H-pyrazole-4-carboxylic acid [2-(2,4-dichlorophenyl)-2-methoxy-1-methyl-ethyl]-amide A solution of 3-difluoromethyl-1-methyl-1H-pyrazole-4-carbonyl chloride (195 mg, 1.0 mmol) in dichloromethane (2 ml) was added dropwise to a stirred solution of (234 mg, 1.0 mmol) 2-(2,4-dichloro-phenyl)-2-methoxy-1-methyl-ethylamine, which was prepared as described in example P2, and triethylamine (202 mg, 2.0 mmol) in dichloromethane (6 ml) at 0° C. The reaction mixture was stirred for 1 hr at ambient temperature then allowed to stand for 4 h. After removal of the solvent the residue was purified by flash chromatography over silica gel (eluant:hexane/ethyl acetate 1:1). 170 mg (43% of theory) of 3-difluoromethyl-1-methyl-1H-pyrazole-4-carboxylic acid [2-(2,4-dichlorophenyl)-2-methoxy-1-methyl-ethyl]-amide was obtained in the form of a resin as a mixture of diastereomeres.

$^1$H NMR (400 MHz, CDCl$_3$): δ 1.01+1.36 (2 d, 3H, CH$_3$), 3.31 (s, 3H, NCH$_3$), 3.88+3.92 (2 s, 3H, CH$_3$), 4.41-4.46+4.51-4.56 (2 m, 1H, CH), 4.60+4.69 (2 d, 1H, CH), 6.63+6.83 (2 m$_{broad}$, 1H, NH), 6.70-7.00 (2 t, 1H, CHF$_2$), 7.17-7.41 (m, 3H, Ar—H), 7.80+7.93 (2 s, 1H, pyrazole-H).

MS [M+H]$^+$ 392/394/396.

Example P2

Preparation of 2-(2,4-dichlorophenyl)-2-methoxy-1-methyl-ethylamine a) Preparation of 2,4-dichloro-1-((E)-2-nitro-propenyl)-benzene

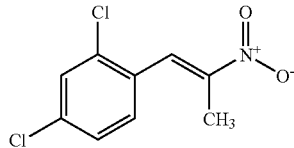

In a sulfonation flask 2,4-dichloro-benzaldehyde (77 g, 0.44 mol), nitroethane (216 ml, 3.04 mol) and ammonium acetate (81.4 g, 1.06 mol) were added to glacial acetic acid (600 ml). The resulting solution was heated to 90° C. for three hours. After removal of the solvent ice-water (400 ml) was added. The solid product was collected by filtration, washed with water and recrystallized from ethanol. 55.9 g (55% of theory) of 2,4-dichloro-1-((E)-2-nitro-propenyl)-benzene was obtained in the form of a yellow solid (m.p. 79-81° C.).

$^1$H NMR (400 MHz, CDCl$_3$): δ 8.11 (s, 1H), 7.51 (d, 1H), 7.34 (dd, 1H), 7.27 (d, 1H), 2.33 (s, 3H, CH$_3$).

b) Preparation of 2,4-dichloro-1-(1-methoxy-2-nitro-propyl)-benzene

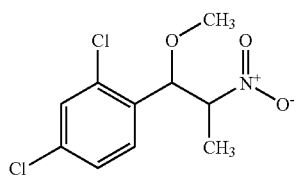

To a stirred yellow solution of the 2,4-dichloro-1-((E)-2-nitro-propenyl)-benzene (4 mmol, 0.93 g), in dry toluene (20 ml) under $N_2$ was added at 0° C. dropwise during 2' a mixture of 5.4M CH3ONa in methanol (16.2 mmol, 3 ml) and methanol (2 ml). After stirring for 1.5 h glacial acid (3 ml) was added, followed by water (20 ml). The aqueous solution was extracted with dichloromethane (2×30 ml), the organic layers were combined, dried (MgSO$_4$), filtered, and evaporated under reduced pressure to give 0.78 g crude 1-aryl-1-methoxy-2-nitropropane a yellow oil. This raw material is purified by column chromatography (silicagel, hexane/ethylacetate 8:2) to afford 0.45 g (43% of theory) of 2,4-dichloro-1-(1-methoxy-2-nitro-propyl)-benzene in the form of liquid, as a mixture of diastereomers.

$^1$H NMR (400 MHz, CDCl$_3$): δ 1.35-1.37+1.39-1.40 (2 d, 3H, CH$_3$), 3.18+3.21 (2 s, 3H, CH$_3$), 3.88+3.92 (2 s, 3H, CH$_3$), 4.69-4.75 (m, 1H, CH), 5.16-5.18+5.39-5.40 (2 d, 1H, CH), 7.15-7.47 (m, 3H, Ar—H).

MS [M+H]$^+$ 264/266/268.

c) Preparation of 2-(2,4-dichlorophenyl)-2-methoxy-1-methyl-ethylamine

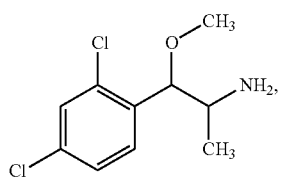

2,4-dichloro-1-(1-methoxy-2-nitro-propyl)-benzene (0.35 g, 1.32 mmol), was dissolved with i-PrOH (27 ml) and treated with 1N HCl (13.2 ml, 13.2 mmol). Zinc dust (1.73 g, 26.4 mmol) was then added in small portions over 15 minutes and the solution allowed to stir for two hours at ambient temperature. The suspension was quenched by addition of saturated NaHCO3 (45 ml), stirred for 15 minutes and filtered through a small plug of Celite, washing with ethylacetate (40 ml). The organic extract was dried over anhydrous MgSO4, filtered and the solvent was removed under reduced pressure. 240 mg (77.6% of theory) of 2-(2,4-dichlorophenyl)-2-methoxy-1-methyl-ethylamine (compound Z1.14) was obtained in the form of a colourless oil as a mixture of diastereomeres.

$^1$H NMR (400 MHz, CDCl$_3$): δ 1.01+1.19 (2 d, 3H, CH$_3$), 2.20 (s$_{broad}$, 2H, NH$_2$) 3.19+3.25 (2 s, 3H, CH$_3$), 4.06+4.12 (2 q, 1H, CH), 4.38-4.53 (2 d, 1H, CH), 7.29-7.38 (m, 3H, Ar—H).

MS [M+H]$^+$ 234/236/238.

The 2-(2,4-dichlorophenyl)-2-methoxy-1-methyl-ethylamine was used in example P1 without further purification.

c2) Preparation of 2-(2,4-dichlorophenyl)-2-methoxy-1-methyl-ethylamine

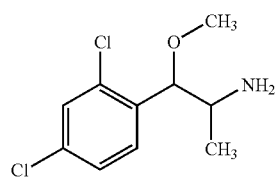

2,4-dichloro-1-(1-methoxy-2-nitro-propyl)-benzene (132.2 g, 0.500 mol), was dissolved in THF (3.6 l). The solution was deaerated, RaNi-EtOH (133 g) catalyst was added, and the mixture was hydrogenated at 50 bar at ambient temperature for 23 hours. The catalyst was removed by filtration and the solvent was removed under reduced pressure. 117.1 g (100% of theory) of 2-(2,4-dichlorophenyl)-2-methoxy-1-methyl-ethylamine (compound Z1.14) was obtained in the form of a colourless oil as a mixture of diastereomeres.

$^1$H NMR (400 MHz, CDCl$_3$): δ 1.01+1.19 (2 d, 3H, CH$_3$), 2.20 (s$_{broad}$, 2H, NH$_2$) 3.19+3.25 (2 s, 3H, CH$_3$), 4.06+4.12 (2 q, 1H, CH), 4.38-4.53 (2 d, 1H, CH), 7.29-7.38 (m, 3H, Ar—H).

MS [M+H]$^+$ 234/236/238.

Example P3

Preparation of 3-difluoromethyl-1-methyl-1H-pyrazole-4-carboxylic acid [2-(2,4-dichlorophenyl)-2-methoxyamino-1-methyl-ethyl]-amide (Compound No. 1.76)

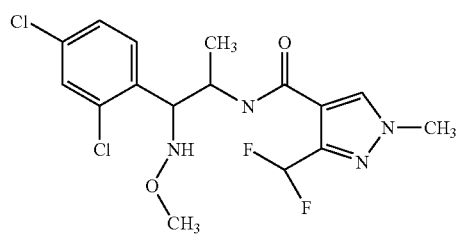

a) Preparation of 3-difluoromethyl-1-methyl-1H-pyrazole-4-carboxylic acid [2-(2,4-dichlorophenyl)-2-methoxyamino-1-methyl-ethyl]-amide A solution of 3-difluoromethyl-1-methyl-1H-pyrazole-4-carbonyl chloride (86 mg, 0.44 mmol) in dichloromethane (1 ml) was added dropwise to a stirred solution of (110 mg, 0.44 mmol) 2-(2,4-dichloro-phenyl)-2-methoxyamino-1-methyl-ethylamine, which was prepared as described in example P4, and triethylamine (50 mg, 0.50 mmol) in dichloromethane (3 ml) at 0° C. The reaction mixture was stirred for 1 hr at ambient temperature then allowed to stand for 1 h. After removal of the solvent the residue was purified by flash chromatography over silica gel (eluant:hexane/ethyl acetate 3:7). 115 mg (64.1% of theory) of 3-difluoromethyl-1-methyl-1H-pyrazole-4-carboxylic acid [2-(2,4-dichlorophenyl)-2-methoxyamino-1-methyl-ethyl]-amide was obtained in the form of a resin as a mixture of diastereomeres.

$^1$H NMR (400 MHz, CDCl$_3$): δ 1.17+1.20 (2 d, 3H, CH$_3$), 3.34+3.50 (2 s, 3H, NCH$_3$), 3.90+3.91 (2 s, 3H$_2$OCH$_3$), 4.41-4.46+4.61-4.65 (2 m, 1H, CH), 4.59+4.69 (2 d, 1H, CH), 6.60+6.73 (2 m$_{broad}$, 1H, NH), 6.66-6.93+6.74-7.02 (2 t, 1H, CHF$_2$), 7.23-7.28 (m, 1H, Ar—H), 7.38-7.40 (m, 1H, Ar—H), 7.48+7.50 (2 d, 1H, Ar—H), 7.89+7.91 (2 s, 1H, pyrazole-H).

MS [M+H]$^+$ 405/407.

Example P4

Preparation of 2-(2,4-dichloro-phenyl)-2-methoxyamino-1-methyl-ethylamine b) Preparation of N-[1-(2,4-dichloro-phenyl)-2-nitropropyl]-O-methyl-hydroxylamine

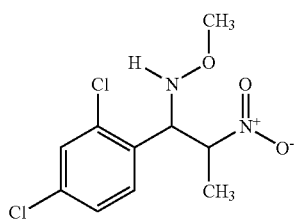

To a stirred yellow solution of the 2,4-dichloro-1-((E)-2-nitro-propenyl)-benzene (1.0 mmol, 0.232 g), in methanol (3 ml) under $N_2$ was added at 0° C. O-methylhydroxylamine hydrochloride (2.0 mmol, 0.167 g) and triethylamine (3.0 mmol, 0.30 g). After stirring for 0.5 h at 50° C., the colourless liquid cooled to ambient temperature and water (20 ml) was added. The aqueous solution was extracted with dichloromethane (20 ml), the organic layers were combined, dried ($MgSO_4$), filtered, and evaporated under reduced pressure to afford 0.23 g (82.4% of theory) of N-[1-(2,4-dichloro-phenyl)-2-nitro-propyl]-O-methyl-hydroxylamine in the form of liquid, as a mixture of diastereomeres.

$^1$H NMR (400 MHz, $CDCl_3$): δ 1.39+1.35 (2 d, 3H, $CH_3$), 3.45+3.52 (2 s, 3H, $CH_3$), 4.96-5.07 (m, 2H, 2×CH), ~0.63 ($m_{broad}$, 1H, NH), 7.26-7.46 (m, 3H, Ar—H).

MS $[M+H]^+$ 279/281.

c) Preparation of N-[2-Amino-1-(2,4-dichloro-phenyl)-propyl]-O-methyl-hydroxylamine

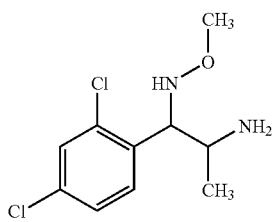

N-[1-(2,4-dichloro-phenyl)-2-nitro-propyl]-O-methyl-hydroxylamine (0.123 g, 0.44 mmol), was dissolved with i-PrOH (9 ml) and treated with 1N HCl (4.4 ml, 4.4 mmol). Zinc dust (0.58 g, 8.8 mmol) was then added in small portions over 15 minutes and the solution allowed to stir for two hours at ambient temperature. The suspension was quenched by addition of saturated $NaHCO_3$ (15 ml), stirred for 15 minutes and filtered through a small plug of Celite, washing with ethylacetate (40 ml). The organic extract was separated, dried over anhydrous $MgSO_4$ an filtered and the solvent was removed under reduced pressure. 110 mg (100% of theory) of N-[2-Amino-1-(2,4-dichloro-phenyl)-propyl]-O-methyl-hydroxylamine (compound Z1.14) was obtained in the form of a colourless oil as a mixture of diastereomeres.

$^1$H NMR (400 MHz, $CDCl_3$): δ 0.97+0.99 (2 d, 3H, $CH_3$), 2.00 ($s_{broad}$, 2H, $NH_2$) 3.06-3.13+3.33-3.40 (2 m, 1H, CH), 3.38+3.48 (2 s, 3H, $CH_3$), 4.25+4.43 (2 d, 1H, CH), ~6.1 ($s_{broad}$, 1H, NH), 7.24-7.58 (m, 3H, Ar—H).

MS $[M+H]^+$ 249/251.

The N-[2-Amino-1-(2,4-dichloro-phenyl)-propyl]-O-methyl-hydroxylamine was used in example P3 without further purification.

Tables 1 and 2: Compounds of Formula IA

The invention is further illustrated by the preferred individual compounds of formula (IA) listed below in Tables 1 and 2. Characterising data is given in Table 4.

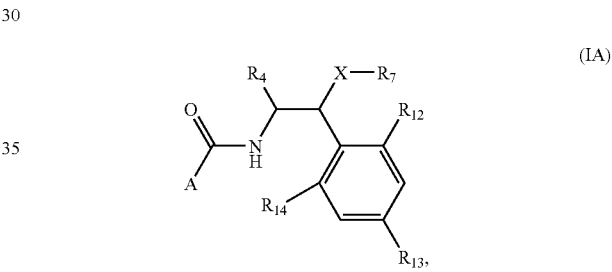

(IA)

Each of Table 1 and 2, which follow Table Y below, comprises 98 compounds of the formula (IA) in which $R_4$, X, $R_7$, $R_{12}$, $R_{13}$ and $R_{14}$ have the values given in Table Y and A has the value given in the relevant Table 1 and 2. Thus Table 1 corresponds to Table Y when Y is 1 and A has the value given under the Table 1 heading and Table 2 corresponds to Table Y when Y is 2 and A has the value given under the Table 2 heading.

TABLE Y

| Comp. No. | R4 | X | R7 | R12 | R13 | R14 |
|---|---|---|---|---|---|---|
| Y.01 | H | —O— | $CH_3$ | 2-Cl | H | H |
| Y.02 | H | —O— | $CH_3$ | 2-Cl | 4-Cl | H |
| Y.03 | H | —O— | $CH_3$ | 2-Cl | 4-Cl | 6-Cl |
| Y.04 | H | —O— | $CH_2CH_3$ | 2-Cl | H | H |
| Y.05 | H | —O— | $CH_2CH_3$ | 2-Cl | 4-Cl | H |
| Y.06 | H | —O— | $CH_2CH_3$ | 2-Cl | 4-Cl | 6-Cl |
| Y.07 | H | —O— | $CH_2CH=CH_2$ | 2-Cl | H | H |
| Y.08 | H | —O— | $CH_2CH=CH_2$ | 2-Cl | 4-Cl | H |
| Y.09 | H | —O— | $CH_2CH=CH_2$ | 2-Cl | 4-Cl | 6-Cl |
| Y.10 | H | —O— | $CH_2C\equiv CH$ | 2-Cl | H | H |
| Y.11 | H | —O— | $CH_2C\equiv CH$ | 2-Cl | 4-Cl | H |
| Y.12 | H | —O— | $CH_2C\equiv CH$ | 2-Cl | 4-Cl | 6-Cl |
| Y.13 | $CH_3$ | —O— | $CH_3$ | 2-Cl | H | H |
| Y.14 | $CH_3$ | —O— | $CH_3$ | 2-Cl | 4-Cl | H |
| Y.15 | $CH_3$ | —O— | $CH_3$ | 2-Cl | 4-Cl | 6-Cl |

TABLE Y-continued

| Comp. No. | R4 | X | R₇ | R₁₂ | R₁₃ | R₁₄ |
|---|---|---|---|---|---|---|
| Y.16 | CH₃ | —O— | H₂CH=CH₂ | 2-Cl | 4-Cl | H |
| Y.17 | CH₃ | —O— | H₂CH=CH₂ | 2-Cl | 4-Cl | 6-Cl |
| Y.18 | CH₃ | —O— | CH₂C≡CH | 2-Cl | 4-Cl | H |
| Y.19 | CH₃ | —O— | CH₂C≡CH | 2-Cl | 4-Cl | 6-Cl |
| Y.20 | CH₃ | —O— | CH₃ | 2-Cl | 4-CF₃ | 6-Cl |
| Y.21 | CH₃ | —O— | CH₂CH=CH₂ | 2-Cl | 4-CF₃ | 6-Cl |
| Y.22 | CH₃ | —O— | CH₂C≡CH | 2-Cl | 4-CF₃ | 6-Cl |
| Y.23 | CH₃ | —O— | CH₃ | 2-Cl | 4-Br | 6-Cl |
| Y.24 | CH₃ | —O— | H₂CH=CH₂ | 2-Cl | 4-Br | 6-Cl |
| Y.25 | CH₃ | —O— | CH₂C≡CH | 2-Cl | 4-Br | 6-Cl |
| Y.26 | CH₃ | —O— | CH₃ | 2-Cl | 4-C≡CH | 6-Cl |
| Y.27 | CH₃ | —O— | H₂CH=CH₂ | 2-Cl | 4-C≡CH | 6-Cl |
| Y.28 | CH₃ | —O— | CH₂C≡CH | 2-Cl | 4-C≡CH | 6-Cl |
| Y.29 | CH₃ | —O— | CH₃ | 2-Cl | 4-CH=NOCH₃ | 6-Cl |
| Y.30 | CH₃ | —O— | CH₂CH=CH₂ | 2-Cl | 4-CH=NOCH₃ | 6-Cl |
| Y.31 | CH₃ | —O— | CH₂C≡CH | 2-Cl | 4-CH=NOCH₃ | 6-Cl |
| Y.32 | CH₃ | —O— | CH₃ | 2-Cl | 4-Cl | 6-CH₃ |
| Y.33 | CH₃ | —O— | H₂CH=CH₂ | 2-Cl | 4-Cl | 6-CH₃ |
| Y.34 | CH₃ | —O— | CH₂C≡CH | 2-Cl | 4-Cl | 6-CH₃ |
| Y.35 | H | —S— | CH₃ | 2-Cl | 4-Cl | H |
| Y.36 | H | —S— | CH₃ | 2-Cl | 4-Cl | 6-Cl |
| Y.37 | H | —S— | CH₂CH₃ | 2-Cl | 4-Cl | H |
| Y.38 | H | —S— | CH₂CH₃ | 2-Cl | 4-Cl | 6-Cl |
| Y.39 | CH₃ | —S— | CH₃ | 2-Cl | 4-Cl | H |
| Y.40 | CH₃ | —S— | CH₃ | 2-Cl | 4-Cl | 6-Cl |
| Y.41 | CH₃ | —S— | CH₂CH₃ | 2-Cl | 4-Cl | H |
| Y.42 | CH₃ | —S— | CH₂CH₃ | 2-Cl | 4-Cl | 6-Cl |
| Y.43 | CH₃ | —S— | CH₃ | 2-Cl | 4-CF₃ | 6-Cl |
| Y.44 | CH₃ | —S— | CH₃ | 2-Cl | 4-Br | 6-Cl |
| Y.45 | CH₃ | —S— | CH₃ | 2-Cl | 4-C≡CH | 6-Cl |
| Y.46 | CH₃ | —S— | CH₃ | 2-Cl | 4-CH=NOCH₃ | 6-Cl |
| Y.47 | CH₃ | —S— | CH₃ | 2-Cl | 4-Cl | 6-CH₃ |
| Y.48 | H | —N(H)— | CH₃ | 2-Cl | 4-Cl | H |
| Y.49 | H | —N(H)— | CH₃ | 2-Cl | 4-Cl | 6-Cl |
| Y.50 | H | —N(H)— | CH₂CH₃ | 2-Cl | 4-Cl | H |
| Y.51 | H | —N(H)— | CH₂CH₃ | 2-Cl | 4-Cl | 6-Cl |
| Y.52 | CH₃ | —N(H)— | CH₃ | 2-Cl | 4-Cl | H |
| Y.53 | CH₃ | —N(H)— | CH₃ | 2-Cl | 4-Cl | 6-Cl |
| Y.54 | CH₃ | —N(H)— | CH₂CH₃ | 2-Cl | 4-Cl | H |
| Y.55 | CH₃ | —N(H)— | CH₂CH₃ | 2-Cl | 4-Cl | 6-Cl |
| Y.56 | CH₃ | —N(H)— | CH₃ | 2-Cl | 4-CF₃ | 6-Cl |
| Y.57 | CH₃ | —N(H)— | CH₃ | 2-Cl | 4-Br | 6-Cl |
| Y.58 | CH₃ | —N(H)— | CH₃ | 2-Cl | 4-C≡CH | 6-Cl |
| Y.59 | CH₃ | —N(H)— | CH₃ | 2-Cl | 4-CH=NOCH₃ | 6-Cl |
| Y.60 | CH₃ | —N(H)— | CH₃ | 2-Cl | 4-Cl | 6-CH₃ |
| Y.61 | H | —N(CH₃)— | CH₃ | 2-Cl | 4-Cl | H |
| Y.62 | H | —N(CH₃)— | CH₃ | 2-Cl | 4-Cl | 6-Cl |
| Y.63 | H | —N(CH₃)— | CH₂CH₃ | 2-Cl | 4-Cl | H |
| Y.64 | H | —N(CH₃)— | CH₂CH₃ | 2-Cl | 4-Cl | 6-Cl |
| Y.65 | CH₃ | —N(CH₃)— | CH₃ | 2-Cl | 4-Cl | H |
| Y.66 | CH₃ | —N(CH₃)— | CH₃ | 2-Cl | 4-Cl | 6-Cl |
| Y.67 | CH₃ | —N(CH₃)— | CH₂CH₃ | 2-Cl | 4-Cl | H |
| Y.68 | CH₃ | —N(CH₃)— | CH₂CH₃ | 2-Cl | 4-Cl | 6-Cl |
| Y.69 | CH₃ | —N(CH₃)— | CH₃ | 2-Cl | 4-CF₃ | 6-Cl |
| Y.70 | CH₃ | —N(CH₃)— | CH₃ | 2-Cl | 4-Br | 6-Cl |
| Y.71 | CH₃ | —N(CH₃)— | CH₃ | 2-Cl | 4-C≡CH | 6-Cl |
| Y.72 | CH₃ | —N(CH₃)— | CH₃ | 2-Cl | 4-CH=NOCH₃ | 6-Cl |
| Y.73 | CH₃ | —N(CH₃)— | CH₃ | 2-Cl | 4-Cl | 6-CH₃ |
| Y.74 | H | —N(H)O— | CH₃ | 2-Cl | 4-Cl | H |
| Y.75 | H | —N(H)O— | CH₃ | 2-Cl | 4-Cl | 6-Cl |
| Y.76 | CH₃ | —N(H)O— | CH₃ | 2-Cl | 4-Cl | H |
| Y.77 | CH₃ | —N(H)O— | CH₃ | 2-Cl | 4-Cl | 6-Cl |
| Y.78 | CH₃ | —N(H)O— | CH₃ | 2-Cl | 4-CF₃ | 6-Cl |
| Y.79 | CH₃ | —N(H)O— | CH₃ | 2-Cl | 4-Br | 6-Cl |
| Y.80 | CH₃ | —N(H)O— | CH₃ | 2-Cl | 4-C≡CH | 6-Cl |
| Y.81 | CH₃ | —N(H)O— | CH₃ | 2-Cl | 4-CH=NOCH₃ | 6-Cl |
| Y.82 | CH₃ | —N(H)O— | CH₃ | 2-Cl | 4-Cl | 6-CH₃ |
| Y.83 | H | —N(CH₃)O— | CH₃ | 2-Cl | 4-Cl | H |
| Y.84 | H | —N(CH₃)O— | CH₃ | 2-Cl | 4-Cl | 6-Cl |
| Y.85 | H | —N(CH₃)O— | CH₂CH₃ | 2-Cl | 4-Cl | H |
| Y.86 | H | —N(CH₃)O— | CH₂CH₃ | 2-Cl | 4-Cl | 6-Cl |
| Y.87 | CH₃ | —N(CH₃)O— | CH₃ | 2-Cl | 4-Cl | H |
| Y.88 | CH₃ | —N(CH₃)O— | CH₃ | 2-Cl | 4-Cl | 6-Cl |
| Y.89 | CH₃ | —N(CH₃)O— | CH₂CH₃ | 2-Cl | 4-Cl | H |
| Y.90 | CH₃ | —N(CH₃)O— | CH₂CH₃ | 2-Cl | 4-Cl | 6-Cl |

TABLE Y-continued

| Comp. No. | R4 | X | R7 | R12 | R13 | R14 |
|---|---|---|---|---|---|---|
| Y.91 | CH$_3$ | —N(CH$_3$)O— | CH$_3$ | 2-Cl | 4-CF$_3$ | 6-Cl |
| Y.92 | CH$_3$ | —N(CH$_3$)O— | CH$_3$ | 2-Cl | 4-Br | 6-Cl |
| Y.93 | CH$_3$ | —N(CH$_3$)O— | CH$_3$ | 2-Cl | 4-C≡CH | 6-Cl |
| Y.94 | CH$_3$ | —N(CH$_3$)O— | CH$_3$ | 2-Cl | 4-CH=NOCH$_3$ | 6-Cl |
| Y.95 | CH$_3$ | —N(CH$_3$)O— | CH$_3$ | 2-Cl | 4-Cl | 6-CH$_3$ |
| Y.96 | CH$_3$ | —O— | CH$_2$CH$_3$ | 2-Cl | H | H |
| Y.97 | CH$_3$ | —O— | CH$_2$CH$_3$ | 2-Cl | 4-Cl | H |
| Y.98 | CH$_3$ | —O— | CH$_2$CH$_3$ | 2-Cl | 4-Cl | 6-Cl |

Table 1 provides 98 compounds of formula (IA), wherein A is

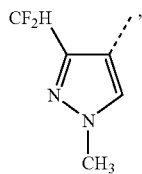

wherein the dashed lines indicate the point of attachment of the group A to the amide group, and R$_4$, X, R$_7$, R$_{12}$, R$_{13}$ and R$_{14}$ are as defined in Table Y. For example, compound 1.14 has the following structure:

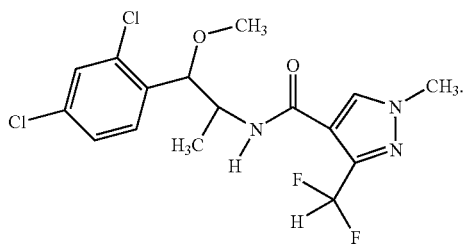

(1.14)

Table 2 provides 98 compounds of formula (IA) wherein A is

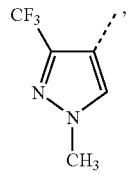

wherein the dashed lines indicate the point of attachment of the group A to the amide group, and R$_4$, X, R$_7$, R$_{12}$, R$_{13}$ and R$_{14}$ are as defined in Table Y.

Table 3: Compounds of Formula IIA

The invention is further illustrated by the preferred individual compounds of formula (IIA) listed below in Table 3.

TABLE 3

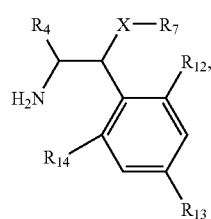

(IIA)

| Comp. No. | R4 | X | R7 | R12 | R13 | R14 |
|---|---|---|---|---|---|---|
| Z1.01 | H | —O— | CH$_3$ | 2-Cl | H | H |
| Z1.02 | H | —O— | CH$_3$ | 2-Cl | 4-Cl | H |
| Z1.03 | H | —O— | CH$_3$ | 2-Cl | 4-Cl | 6-Cl |
| Z1.04 | H | —O— | CH$_2$CH$_3$ | 2-Cl | H | H |
| Z1.05 | H | —O— | CH$_2$CH$_3$ | 2-Cl | 4-Cl | H |
| Z1.06 | H | —O— | CH$_2$CH$_3$ | 2-Cl | 4-Cl | 6-Cl |
| Z1.07 | H | —O— | CH$_2$CH=CH$_2$ | 2-Cl | H | H |
| Z1.08 | H | —O— | CH$_2$CH=CH$_2$ | 2-Cl | 4-Cl | H |
| Z1.09 | H | —O— | CH$_2$CH=CH$_2$ | 2-Cl | 4-Cl | 6-Cl |
| Z1.10 | H | —O— | CH$_2$C≡CH | 2-Cl | H | H |
| Z1.11 | H | —O— | CH$_2$C≡CH | 2-Cl | 4-Cl | H |
| Z1.12 | H | —O— | CH$_2$C≡CH | 2-Cl | 4-Cl | 6-Cl |
| Z1.13 | CH$_3$ | —O— | CH$_3$ | 2-Cl | H | H |
| Z1.14 | CH$_3$ | —O— | CH$_3$ | 2-Cl | 4-Cl | H |
| Z1.15 | CH$_3$ | —O— | CH$_3$ | 2-Cl | 4-Cl | 6-Cl |
| Z1.16 | CH$_3$ | —O— | H$_2$C=CH$_2$ | 2-Cl | 4-Cl | H |
| Z1.17 | CH$_3$ | —O— | H$_2$CH=CH$_2$ | 2-Cl | 4-Cl | 6-Cl |

TABLE 3-continued

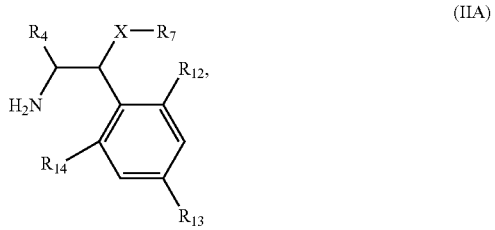
(IIA)

| Comp. No. | $R_4$ | X | $R_7$ | $R_{12}$ | $R_{13}$ | $R_{14}$ |
|---|---|---|---|---|---|---|
| Z1.18 | CH$_3$ | —O— | CH$_2$C≡CH | 2-Cl | 4-Cl | H |
| Z1.19 | CH$_3$ | —O— | CH$_2$C≡CH | 2-Cl | 4-Cl | 6-Cl |
| Z1.20 | CH$_3$ | —O— | CH$_3$ | 2-Cl | 4-CF$_3$ | 6-Cl |
| Z1.21 | CH$_3$ | —O— | CH$_2$CH=CH$_2$ | 2-Cl | 4-CF$_3$ | 6-Cl |
| Z1.22 | CH$_3$ | —O— | CH$_2$C≡CH | 2-Cl | 4-CF$_3$ | 6-Cl |
| Z1.23 | CH$_3$ | —O— | CH$_3$ | 2-Cl | 4-Br | 6-Cl |
| Z1.24 | CH$_3$ | —O— | H$_2$CH=CH$_2$ | 2-Cl | 4-Br | 6-Cl |
| Z1.25 | CH$_3$ | —O— | CH$_2$C≡CH | 2-Cl | 4-Br | 6-Cl |
| Z1.26 | CH$_3$ | —O— | CH$_3$ | 2-Cl | 4-C≡CH | 6-Cl |
| Z1.27 | CH$_3$ | —O— | H$_2$CH=CH$_2$ | 2-Cl | 4-C≡CH | 6-Cl |
| Z1.28 | CH$_3$ | —O— | CH$_2$C≡CH | 2-Cl | 4-C≡CH | 6-Cl |
| Z1.29 | CH$_3$ | —O— | CH$_3$ | 2-Cl | 4-CH=NOCH$_3$ | 6-Cl |
| Z1.30 | CH$_3$ | —O— | CH$_2$CH=CH$_2$ | 2-Cl | 4-CH=NOCH$_3$ | 6-Cl |
| Z1.31 | CH$_3$ | —O— | CH$_2$C≡CH | 2-Cl | 4-CH=NOCH$_3$ | 6-Cl |
| Z1.32 | CH$_3$ | —O— | CH$_3$ | 2-Cl | 4-Cl | 6-CH$_3$ |
| Z1.33 | CH$_3$ | —O— | H$_2$CH=CH$_2$ | 2-Cl | 4-Cl | 6-CH$_3$ |
| Z1.34 | CH$_3$ | —O— | CH$_2$C≡CH | 2-Cl | 4-Cl | 6-CH$_3$ |
| Z1.35 | H | —S— | CH$_3$ | 2-Cl | 4-Cl | H |
| Z1.36 | H | —S— | CH$_3$ | 2-Cl | 4-Cl | 6-Cl |
| Z1.37 | H | —S— | CH$_2$CH$_3$ | 2-Cl | 4-Cl | H |
| Z1.38 | H | —S— | CH$_2$CH$_3$ | 2-Cl | 4-Cl | 6-Cl |
| Z1.39 | CH$_3$ | —S— | CH$_3$ | 2-Cl | 4-Cl | H |
| Z1.40 | CH$_3$ | —S— | CH$_3$ | 2-Cl | 4-Cl | 6-Cl |
| Z1.41 | CH$_3$ | —S— | CH$_2$CH$_3$ | 2-Cl | 4-Cl | H |
| Z1.42 | CH$_3$ | —S— | CH$_2$CH$_3$ | 2-Cl | 4-Cl | 6-Cl |
| Z1.43 | CH$_3$ | —S— | CH$_3$ | 2-Cl | 4-CF$_3$ | 6-Cl |
| Z1.44 | CH$_3$ | —S— | CH$_3$ | 2-Cl | 4-Br | 6-Cl |
| Z1.45 | CH$_3$ | —S— | CH$_3$ | 2-Cl | 4-C≡CH | 6-Cl |
| Z1.46 | CH$_3$ | —S— | CH$_3$ | 2-Cl | 4-CH=NOCH$_3$ | 6-Cl |
| Z1.47 | CH$_3$ | —S— | CH$_3$ | 2-Cl | 4-Cl | 6-CH$_3$ |
| Z1.48 | H | —N(H)— | CH$_3$ | 2-Cl | 4-Cl | H |
| Z1.49 | H | —N(H)— | CH$_3$ | 2-Cl | 4-Cl | 6-Cl |
| Z1.50 | H | —N(H)— | CH$_2$CH$_3$ | 2-Cl | 4-Cl | H |
| Z1.51 | H | —N(H)— | CH$_2$CH$_3$ | 2-Cl | 4-Cl | 6-Cl |
| Z1.52 | CH$_3$ | —N(H)— | CH$_3$ | 2-Cl | 4-Cl | H |
| Z1.53 | CH$_3$ | —N(H)— | CH$_3$ | 2-Cl | 4-Cl | 6-Cl |
| Z1.54 | CH$_3$ | —N(H)— | CH$_2$CH$_3$ | 2-Cl | 4-Cl | H |
| Z1.55 | CH$_3$ | —N(H)— | CH$_2$CH$_3$ | 2-Cl | 4-Cl | 6-Cl |
| Z1.56 | CH$_3$ | —N(H)— | CH$_3$ | 2-Cl | 4-CF$_3$ | 6-Cl |
| Z1.57 | CH$_3$ | —N(H)— | CH$_3$ | 2-Cl | 4-Br | 6-Cl |
| Z1.58 | CH$_3$ | —N(H)— | CH$_3$ | 2-Cl | 4-C≡CH | 6-Cl |
| Z1.59 | CH$_3$ | —N(H)— | CH$_3$ | 2-Cl | 4-CH=NOCH$_3$ | 6-Cl |
| Z1.60 | CH$_3$ | —N(H)— | CH$_3$ | 2-Cl | 4-Cl | 6-CH$_3$ |
| Z1.61 | H | —N(CH$_3$)— | CH$_3$ | 2-Cl | 4-Cl | H |
| Z1.62 | H | —N(CH$_3$)— | CH$_3$ | 2-Cl | 4-Cl | 6-Cl |
| Z1.63 | H | —N(CH$_3$)— | CH$_2$CH$_3$ | 2-Cl | 4-Cl | H |
| Z1.64 | H | —N(CH$_3$)— | CH$_2$CH$_3$ | 2-Cl | 4-Cl | 6-Cl |
| Z1.65 | CH$_3$ | —N(CH$_3$)— | CH$_3$ | 2-Cl | 4-Cl | H |
| Z1.66 | CH$_3$ | —N(CH$_3$)— | CH$_3$ | 2-Cl | 4-Cl | 6-Cl |
| Z1.67 | CH$_3$ | —N(CH$_3$)— | CH$_2$CH$_3$ | 2-Cl | 4-Cl | H |
| Z1.68 | CH$_3$ | —N(CH$_3$)— | CH$_2$CH$_3$ | 2-Cl | 4-Cl | 6-Cl |
| Z1.69 | CH$_3$ | —N(CH$_3$)— | CH$_3$ | 2-Cl | 4-CF$_3$ | 6-Cl |
| Z1.70 | CH$_3$ | —N(CH$_3$)— | CH$_3$ | 2-Cl | 4-Br | 6-Cl |
| Z1.71 | CH$_3$ | —N(CH$_3$)— | CH$_3$ | 2-Cl | 4-C≡CH | 6-Cl |
| Z1.72 | CH$_3$ | —N(CH$_3$)— | CH$_3$ | 2-Cl | 4-CH=NOCH$_3$ | 6-Cl |
| Z1.73 | CH$_3$ | —N(CH$_3$)— | CH$_3$ | 2-Cl | 4-Cl | 6-CH$_3$ |
| Z1.74 | H | —N(H)O— | CH$_3$ | 2-Cl | 4-Cl | H |
| Z1.75 | H | —N(H)O— | CH$_3$ | 2-Cl | 4-Cl | 6-Cl |
| Z1.76 | CH$_3$ | —N(H)O— | CH$_3$ | 2-Cl | 4-Cl | H |
| Z1.77 | CH$_3$ | —N(H)O— | CH$_3$ | 2-Cl | 4-Cl | 6-Cl |
| Z1.78 | CH$_3$ | —N(H)O— | CH$_3$ | 2-Cl | 4-CF$_3$ | 6-Cl |
| Z1.79 | CH$_3$ | —N(H)O— | CH$_3$ | 2-Cl | 4-Br | 6-Cl |
| Z1.80 | CH$_3$ | —N(H)O— | CH$_3$ | 2-Cl | 4-C≡CH | 6-Cl |

TABLE 3-continued

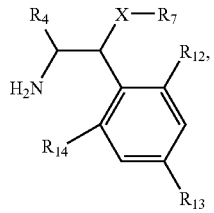

(IIA)

| Comp. No. | R$_4$ | X | R$_7$ | R$_{12}$ | R$_{13}$ | R$_{14}$ |
|---|---|---|---|---|---|---|
| Z1.81 | CH$_3$ | —N(H)O— | CH$_3$ | 2-Cl | 4-CH=NOCH$_3$ | 6-Cl |
| Z1.82 | CH$_3$ | —N(H)O— | CH$_3$ | 2-Cl | 4-Cl | 6-CH$_3$ |
| Z1.83 | H | —N(CH$_3$)O— | CH$_3$ | 2-Cl | 4-Cl | H |
| Z1.84 | H | —N(CH$_3$)O— | CH$_3$ | 2-Cl | 4-Cl | 6-Cl |
| Z1.85 | H | —N(CH$_3$)O— | CH$_2$CH$_3$ | 2-Cl | 4-Cl | H |
| Z1.86 | H | —N(CH$_3$)O— | CH$_2$CH$_3$ | 2-Cl | 4-Cl | 6-Cl |
| Z1.87 | CH$_3$ | —N(CH$_3$)O— | CH$_3$ | 2-Cl | 4-Cl | H |
| Z1.88 | CH$_3$ | —N(CH$_3$)O— | CH$_3$ | 2-Cl | 4-Cl | 6-Cl |
| Z1.89 | CH$_3$ | —N(CH$_3$)O— | CH$_2$CH$_3$ | 2-Cl | 4-Cl | H |
| Z1.90 | CH$_3$ | —N(CH$_3$)O— | CH$_2$CH$_3$ | 2-Cl | 4-Cl | 6-Cl |
| Z1.91 | CH$_3$ | —N(CH$_3$)O— | CH$_3$ | 2-Cl | 4-CF$_3$ | 6-Cl |
| Z1.92 | CH$_3$ | —N(CH$_3$)O— | CH$_3$ | 2-Cl | 4-Br | 6-Cl |
| Z1.93 | CH$_3$ | —N(CH$_3$)O— | CH$_3$ | 2-Cl | 4-C≡CH | 6-Cl |
| Z1.94 | CH$_3$ | —N(CH$_3$)O— | CH$_3$ | 2-Cl | 4-CH=NOCH$_3$ | 6-Cl |
| Z1.95 | CH$_3$ | —N(CH$_3$)O— | CH$_3$ | 2-Cl | 4-Cl | 6-CH$_3$ |
| Z1.96 | CH3 | —O— | CH2CH3 | 2-Cl | H | H |
| Z1.97 | CH3 | —O— | CH2CH3 | 2-Cl | 4-Cl | H |
| Z1.98 | CH3 | —O— | CH2CH3 | 2-Cl | 4-Cl | 6-Cl |

Table 4: Characterising Data

Table 4 shows selected melting point and selected NMR data for compounds of Tables 1 and 2. CDCl$_3$ was used as the solvent for NMR measurements, unless otherwise stated. If a mixture of solvents was present, this is indicated as, for example: CDCl$_3$/d$_6$-DMSO). No attempt is made to list all characterising data in all cases.

In Table 4 and throughout the description that follows, temperatures are given in degrees Celsius; "NMR" means nuclear magnetic resonance spectrum; MS stands for mass spectrum; "%" is percent by weight, unless corresponding concentrations are indicated in other units. The following abbreviations are used throughout this description:

| | |
|---|---|
| m.p. = melting point | b.p. = boiling point. |
| S = singlet | br = broad |
| d = doublet | dd = doublet of doublets |
| t = triplet | q = quartet |
| m = multiplet | ppm = parts per million |

| Compound No. | 1H-NMR data: ppm (multiplicity/number of Hs) | MS [M + H]$^+$ | m.p. (° C.) |
|---|---|---|---|
| 1.01 | — | 344/346 | resin |
| 1.07 | — | 370/372 | resin |
| 1.14 | 1.01 + 1.36(2d, 3H, CH$_3$), 3.31(s, 3H, NCH$_3$), 3.88 + 3.92(2s, 3H, CH$_3$), 4.41-4.46 + 4.51-4.56(2m, 1H, CH), 4.60 + 4.69(2d, 1H, CH), 6.63 + 6.83(2m$_{broad}$, 1H, NH), 6.70-7.00(2t, 1H, CHF$_2$), 7.17-7.41(m, 3H, Ar—H), 7.80 + 7.93(2s, 1H, pyrazole-H). | 392/394/396 | resin |
| 1.15 | 1.23 + 1.27(2d, 3H, CH$_3$), 3.27(s, 3H, NCH$_3$), 3.88 + 3.93(2s, 3H, CH$_3$), 4.71-4.76 + 4.85-4.90(2m, 1H, CH), 4.84 + 4.92(2d, 1H, CH), 6.35 + 6.60(2m$_{broad}$, 1H, NH), 6.77-7.05(2t, 1H, CHF$_2$), 7.30-7.34(m, 2H, Ar—H), 7.78 + 7.83(2s, 1H, pyrazole-H). | 426/428/430 | 130-133 |
| 1.76 | 1.17 + 1.20(2d, 3H, CH$_3$), 3.34 + 3.50(2s, 3H, NCH$_3$), 3.90 + 3.91(2s, 3H, OCH$_3$), 4.41-4.46 + 4.61-4.65(2m, 1H, CH), 4.59 + 4.69(2d, 1H, CH), 6.60 + 6.73(2m$_{broad}$, 1H, NH), 6.66-6.93 + 6.74-7.02(2t, 1H, CHF$_2$), 7.23-7.28(m, 1H, Ar—H), 7.38-7.40(m, 1H, Ar—H), 7.48 + 7.50(2d, 1H, Ar—H), 7.89 + 7.91 (2s, 1H, pyrazole-H).- | 405/407 | resin |
| 2.01 | — | 362/364 | resin |

Tables 1 and 2a: Compounds of Formula IAa

The invention is further illustrated by the preferred individual compounds of formula (IA) listed below in Tables 1 and 2.

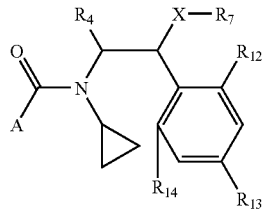

(IAa)

Each of Table 1a and 2a, which follow Table Ya below, comprises 98 compounds of the formula (IAa) in which $R_4$, X, $R_7$, $R_{12}$, $R_{13}$ and $R_{14}$ have the values given in Table Ya and A has the value given in the relevant Table 1a and 2a. Thus Table 1a corresponds to Table Ya when Ya is 1 and A has the value given under the Table 1a heading and Table 2a corresponds to Table Ya when Ya is 2 and A has the value given under the Table 2a heading.

TABLE Ya

| Comp. No. | $R_4$ | X | $R_7$ | $R_{12}$ | $R_{13}$ | $R_{14}$ |
|---|---|---|---|---|---|---|
| Ya.01 | H | —O— | $CH_3$ | 2-Cl | H | H |
| Ya.02 | H | —O— | $CH_3$ | 2-Cl | 4-Cl | H |
| Ya.03 | H | —O— | $CH_3$ | 2-Cl | 4-Cl | 6-Cl |
| Ya.04 | H | —O— | $CH_2CH_3$ | 2-Cl | H | H |
| Ya.05 | H | —O— | $CH_2CH_3$ | 2-Cl | 4-Cl | H |
| Ya.06 | H | —O— | $CH_2CH_3$ | 2-Cl | 4-Cl | 6-Cl |
| Ya.07 | H | —O— | $CH_2CH=CH_2$ | 2-Cl | H | H |
| Ya.08 | H | —O— | $CH_2CH=CH_2$ | 2-Cl | 4-Cl | H |
| Ya.09 | H | —O— | $CH_2CH=CH_2$ | 2-Cl | 4-Cl | 6-Cl |
| Ya.10 | H | —O— | $CH_2C\equiv CH$ | 2-Cl | H | H |
| Ya.11 | H | —O— | $CH_2C\equiv CH$ | 2-Cl | 4-Cl | H |
| Ya.12 | H | —O— | $CH_2C\equiv CH$ | 2-Cl | 4-Cl | 6-Cl |
| Ya.13 | $CH_3$ | —O— | $CH_3$ | 2-Cl | H | H |
| Ya.14 | $CH_3$ | —O— | $CH_3$ | 2-Cl | 4-Cl | H |
| Ya.15 | $CH_3$ | —O— | $CH_3$ | 2-Cl | 4-Cl | 6-Cl |
| Ya.16 | $CH_3$ | —O— | $H_2CH=CH_2$ | 2-Cl | 4-Cl | H |
| Ya.17 | $CH_3$ | —O— | $H_2CH=CH_2$ | 2-Cl | 4-Cl | 6-Cl |
| Ya.18 | $CH_3$ | —O— | $CH_2C\equiv CH$ | 2-Cl | 4-Cl | H |
| Ya.19 | $CH_3$ | —O— | $CH_2C\equiv CH$ | 2-Cl | 4-Cl | 6-Cl |
| Ya.20 | $CH_3$ | —O— | $CH_3$ | 2-Cl | 4-$CF_3$ | 6-Cl |
| Ya.21 | $CH_3$ | —O— | $CH_2CH=CH_2$ | 2-Cl | 4-$CF_3$ | 6-Cl |
| Ya.22 | $CH_3$ | —O— | $CH_2C\equiv CH$ | 2-Cl | 4-$CF_3$ | 6-Cl |
| Ya.23 | $CH_3$ | —O— | $CH_3$ | 2-Cl | 4-Br | 6-Cl |
| Ya.24 | $CH_3$ | —O— | $H_2CH=CH_2$ | 2-Cl | 4-Br | 6-Cl |
| Ya.25 | $CH_3$ | —O— | $CH_2C\equiv CH$ | 2-Cl | 4-Br | 6-Cl |
| Ya.26 | $CH_3$ | —O— | $CH_3$ | 2-Cl | 4-C≡CH | 6-Cl |
| Ya.27 | $CH_3$ | —O— | $H_2CH=CH_2$ | 2-Cl | 4-C≡CH | 6-Cl |
| Ya.28 | $CH_3$ | —O— | $CH_2C\equiv CH$ | 2-Cl | 4-C≡CH | 6-Cl |
| Ya.29 | $CH_3$ | —O— | $CH_3$ | 2-Cl | 4-CH=$NOCH_3$ | 6-Cl |
| Ya.30 | $CH_3$ | —O— | $CH_2CH=CH_2$ | 2-Cl | 4-CH=$NOCH_3$ | 6-Cl |
| Ya.31 | $CH_3$ | —O— | $CH_2C\equiv CH$ | 2-Cl | 4-CH=$NOCH_3$ | 6-Cl |
| Ya.32 | $CH_3$ | —O— | $CH_3$ | 2-Cl | 4-Cl | 6-$CH_3$ |
| Ya.33 | $CH_3$ | —O— | $H_2CH=CH_2$ | 2-Cl | 4-Cl | 6-$CH_3$ |
| Ya.34 | $CH_3$ | —O— | $CH_2C\equiv CH$ | 2-Cl | 4-Cl | 6-$CH_3$ |
| Ya.35 | H | —S— | $CH_3$ | 2-Cl | 4-Cl | H |
| Ya.36 | H | —S— | $CH_3$ | 2-Cl | 4-Cl | 6-Cl |
| Ya.37 | H | —S— | $CH_2CH_3$ | 2-Cl | 4-Cl | H |
| Ya.38 | H | —S— | $CH_2CH_3$ | 2-Cl | 4-Cl | 6-Cl |
| Ya.39 | $CH_3$ | —S— | $CH_3$ | 2-Cl | 4-Cl | H |
| Ya.40 | $CH_3$ | —S— | $CH_3$ | 2-Cl | 4-Cl | 6-Cl |
| Ya.41 | $CH_3$ | —S— | $CH_2CH_3$ | 2-Cl | 4-Cl | H |
| Ya.42 | $CH_3$ | —S— | $CH_2CH_3$ | 2-Cl | 4-Cl | 6-Cl |
| Ya.43 | $CH_3$ | —S— | $CH_3$ | 2-Cl | 4-$CF_3$ | 6-Cl |
| Ya.44 | $CH_3$ | —S— | $CH_3$ | 2-Cl | 4-Br | 6-Cl |
| Ya.45 | $CH_3$ | —S— | $CH_3$ | 2-Cl | 4-C≡CH | 6-Cl |
| Ya.46 | $CH_3$ | —S— | $CH_3$ | 2-Cl | 4-CH=$NOCH_3$ | 6-Cl |
| Ya.47 | $CH_3$ | —S— | $CH_3$ | 2-Cl | 4-Cl | 6-$CH_3$ |
| Ya.48 | H | —N(H)— | $CH_3$ | 2-Cl | 4-Cl | H |
| Ya.49 | H | —N(H)— | $CH_3$ | 2-Cl | 4-Cl | 6-Cl |
| Ya.50 | H | —N(H)— | $CH_2CH_3$ | 2-Cl | 4-Cl | H |
| Ya.51 | H | —N(H)— | $CH_2CH_3$ | 2-Cl | 4-Cl | 6-Cl |
| Ya.52 | $CH_3$ | —N(H)— | $CH_3$ | 2-Cl | 4-Cl | H |
| Ya.53 | $CH_3$ | —N(H)— | $CH_3$ | 2-Cl | 4-Cl | 6-Cl |
| Ya.54 | $CH_3$ | —N(H)— | $CH_2CH_3$ | 2-Cl | 4-Cl | H |
| Ya.55 | $CH_3$ | —N(H)— | $CH_2CH_3$ | 2-Cl | 4-Cl | 6-Cl |
| Ya.56 | $CH_3$ | —N(H)— | $CH_3$ | 2-Cl | 4-$CF_3$ | 6-Cl |
| Ya.57 | $CH_3$ | —N(H)— | $CH_3$ | 2-Cl | 4-Br | 6-Cl |
| Ya.58 | $CH_3$ | —N(H)— | $CH_3$ | 2-Cl | 4-C≡CH | 6-Cl |
| Ya.59 | $CH_3$ | —N(H)— | $CH_3$ | 2-Cl | 4-CH=$NOCH_3$ | 6-Cl |

TABLE Ya-continued

| Comp. No. | R₄ | X | R₇ | R₁₂ | R₁₃ | R₁₄ |
|---|---|---|---|---|---|---|
| Ya.60 | CH₃ | —N(H)— | CH₃ | 2-Cl | 4-Cl | 6-CH₃ |
| Ya.61 | H | —N(CH₃)— | CH₃ | 2-Cl | 4-Cl | H |
| Ya.62 | H | —N(CH₃)— | CH₃ | 2-Cl | 4-Cl | 6-Cl |
| Ya.63 | H | —N(CH₃)— | CH₂CH₃ | 2-Cl | 4-Cl | H |
| Ya.64 | H | —N(CH₃)— | CH₂CH₃ | 2-Cl | 4-Cl | 6-Cl |
| Ya.65 | CH₃ | —N(CH₃)— | CH₃ | 2-Cl | 4-Cl | H |
| Ya.66 | CH₃ | —N(CH₃)— | CH₃ | 2-Cl | 4-Cl | 6-Cl |
| Ya.67 | CH₃ | —N(CH₃)— | CH₂CH₃ | 2-Cl | 4-Cl | H |
| Ya.68 | CH₃ | —N(CH₃)— | CH₂CH₃ | 2-Cl | 4-Cl | 6-Cl |
| Ya.69 | CH₃ | —N(CH₃)— | CH₃ | 2-Cl | 4-CF₃ | 6-Cl |
| Ya.70 | CH₃ | —N(CH₃)— | CH₃ | 2-Cl | 4-Br | 6-Cl |
| Ya.71 | CH₃ | —N(CH₃)— | CH₃ | 2-Cl | 4-C≡CH | 6-Cl |
| Ya.72 | CH₃ | —N(CH₃)— | CH₃ | 2-Cl | 4-CH=NOCH₃ | 6-Cl |
| Ya.73 | CH₃ | —N(CH₃)— | CH₃ | 2-Cl | 4-Cl | 6-CH₃ |
| Ya.74 | H | —N(H)O— | CH₃ | 2-Cl | 4-Cl | H |
| Ya.75 | H | —N(H)O— | CH₃ | 2-Cl | 4-Cl | 6-Cl |
| Ya.76 | CH₃ | —N(H)O— | CH₃ | 2-Cl | 4-Cl | H |
| Ya.77 | CH₃ | —N(H)O— | CH₃ | 2-Cl | 4-Cl | 6-Cl |
| Ya.78 | CH₃ | —N(H)O— | CH₃ | 2-Cl | 4-CF₃ | 6-Cl |
| Ya.79 | CH₃ | —N(H)O— | CH₃ | 2-Cl | 4-Br | 6-Cl |
| Ya.80 | CH₃ | —N(H)O— | CH₃ | 2-Cl | 4-C≡CH | 6-Cl |
| Ya.81 | CH₃ | —N(H)O— | CH₃ | 2-Cl | 4-CH=NOCH₃ | 6-Cl |
| Ya.82 | CH₃ | —N(H)O— | CH₃ | 2-Cl | 4-Cl | 6-CH₃ |
| Ya.83 | H | —N(CH₃)O- | CH₃ | 2-Cl | 4-Cl | H |
| Ya.84 | H | —N(CH₃)O— | CH₃ | 2-Cl | 4-Cl | 6-Cl |
| Ya.85 | H | —N(CH₃)O— | CH₂CH₃ | 2-Cl | 4-Cl | H |
| Ya.86 | H | —N(CH₃)O— | CH₂CH₃ | 2-Cl | 4-Cl | 6-Cl |
| Ya.87 | CH₃ | —N(CH₃)O— | CH₃ | 2-Cl | 4-Cl | H |
| Ya.88 | CH₃ | —N(CH₃)O— | CH₃ | 2-Cl | 4-Cl | 6-Cl |
| Ya.89 | CH₃ | —N(CH₃)O— | CH₂CH₃ | 2-Cl | 4-Cl | H |
| Ya.90 | CH₃ | —N(CH₃)O— | CH₂CH₃ | 2-Cl | 4-Cl | 6-Cl |
| Ya.91 | CH₃ | —N(CH₃)O— | CH₃ | 2-Cl | 4-CF₃ | 6-Cl |
| Ya.92 | CH₃ | —N(CH₃)O— | CH₃ | 2-Cl | 4-Br | 6-Cl |
| Ya.93 | CH₃ | —N(CH₃)O— | CH₃ | 2-Cl | 4-C≡CH | 6-Cl |
| Ya.94 | CH₃ | —N(CH₃)O— | CH₃ | 2-Cl | 4-CH=NOCH₃ | 6-Cl |
| Ya.95 | CH₃ | —N(CH₃)O— | CH₃ | 2-Cl | 4-Cl | 6-CH₃ |
| Ya.96 | CH₃ | —O— | CH₂CH₃ | 2-Cl | H | H |
| Ya.97 | CH₃ | —O— | CH₂CH₃ | 2-Cl | 4-Cl | H |
| Ya.98 | CH₃ | —O— | CH₂CH₃ | 2-Cl | 4-Cl | 6-Cl |

Table 1a provides 98 compounds of formula (IAa), wherein A is

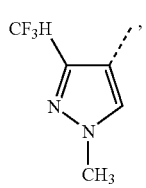

wherein the dashed lines indicate the point of attachment of the group A to the amide group, and $R_4$, X, $R_7$, $R_{12}$, $R_{13}$ and $R_{14}$ are as defined in Table Ya. For example, compound 1a.14 has the following structure:

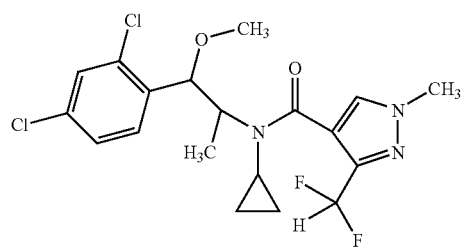

(1a.14)

Table 2a provides 98 compounds of formula (IA) wherein A is

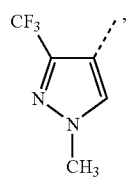

wherein the dashed lines indicate the point of attachment of the group A to the amide group, and $R_4$, X, $R_7$, $R_{12}$, $R_{13}$ and $R_{14}$ are as defined in Table Ya.

Table 3a: Compounds of formula IIAa

The invention is further illustrated by the preferred individual compounds of formula (IIAa) listed below in Table 3.

TABLE 3a (IIAa)

Structure: cyclopropyl-NH-CH(R4)-CH(X-R7)-phenyl with R12, R13, R14 substituents on the phenyl ring.

| Comp. No. | R$_4$ | X | R$_7$ | R$_{12}$ | R$_{13}$ | R$_{14}$ |
|---|---|---|---|---|---|---|
| Z1a.01 | H | —O— | CH$_3$ | 2-Cl | H | H |
| Z1a.02 | H | —O— | CH$_3$ | 2-Cl | 4-Cl | H |
| Z1a.03 | H | —O— | CH$_3$ | 2-Cl | 4-Cl | 6-Cl |
| Z1a.04 | H | —O— | CH$_2$CH$_3$ | 2-Cl | H | H |
| Z1a.05 | H | —O— | CH$_2$CH$_3$ | 2-Cl | 4-Cl | H |
| Z1a.06 | H | —O— | CH$_2$CH$_3$ | 2-Cl | 4-Cl | 6-Cl |
| Z1a.07 | H | —O— | CH$_2$CH=CH$_2$ | 2-Cl | H | H |
| Z1a.08 | H | —O— | CH$_2$CH=CH$_2$ | 2-Cl | 4-Cl | H |
| Z1a.09 | H | —O— | CH$_2$CH=CH$_2$ | 2-Cl | 4-Cl | 6-Cl |
| Z1a.10 | H | —O— | CH$_2$C≡CH | 2-Cl | H | H |
| Z1a.11 | H | —O— | CH$_2$C≡CH | 2-Cl | 4-Cl | H |
| Z1a.12 | H | —O— | CH$_2$C≡CH | 2-Cl | 4-Cl | 6-Cl |
| Z1a.13 | CH$_3$ | —O— | CH$_3$ | 2-Cl | H | H |
| Z1a.14 | CH$_3$ | —O— | CH$_3$ | 2-Cl | 4-Cl | H |
| Z1a.15 | CH$_3$ | —O— | CH$_3$ | 2-Cl | 4-Cl | 6-Cl |
| Z1a.16 | CH$_3$ | —O— | H$_2$CH=CH$_2$ | 2-Cl | 4-Cl | H |
| Z1a.17 | CH$_3$ | —O— | H$_2$CH=CH$_2$ | 2-Cl | 4-Cl | 6-Cl |
| Z1a.18 | CH$_3$ | —O— | CH$_2$C≡CH | 2-Cl | 4-Cl | H |
| Z1a.19 | CH$_3$ | —O— | CH$_2$C≡CH | 2-Cl | 4-Cl | 6-Cl |
| Z1a.20 | CH$_3$ | —O— | CH$_3$ | 2-Cl | 4-CF$_3$ | 6-Cl |
| Z1a.21 | CH$_3$ | —O— | CH$_2$CH=CH$_2$ | 2-Cl | 4-CF$_3$ | 6-Cl |
| Z1a.22 | CH$_3$ | —O— | CH$_2$C≡CH | 2-Cl | 4-CF$_3$ | 6-Cl |
| Z1a.23 | CH$_3$ | —O— | CH$_3$ | 2-Cl | 4-Br | 6-Cl |
| Z1a.24 | CH$_3$ | —O— | H$_2$CH=CH$_2$ | 2-Cl | 4-Br | 6-Cl |
| Z1a.25 | CH$_3$ | —O— | CH$_2$C≡CH | 2-Cl | 4-Br | 6-Cl |
| Z1a.26 | CH$_3$ | —O— | CH$_3$ | 2-Cl | 4-C≡CH | 6-Cl |
| Z1a.27 | CH$_3$ | —O— | H$_2$CH=CH$_2$ | 2-Cl | 4-C≡CH | 6-Cl |
| Z1a.28 | CH$_3$ | —O— | CH$_2$C≡CH | 2-Cl | 4-C≡CH | 6-Cl |
| Z1a.29 | CH$_3$ | —O— | CH$_3$ | 2-Cl | 4-CH=NOCH$_3$ | 6-Cl |
| Z1a.30 | CH$_3$ | —O— | CH$_2$CH=CH$_2$ | 2-Cl | 4-CH=NOCH$_3$ | 6-Cl |
| Z1a.31 | CH$_3$ | —O— | CH$_2$C≡CH | 2-Cl | 4-CH=NOCH$_3$ | 6-Cl |
| Z1a.32 | CH$_3$ | —O— | CH$_3$ | 2-Cl | 4-Cl | 6-CH$_3$ |
| Z1a.33 | CH$_3$ | —O— | H$_2$CH=CH$_2$ | 2-Cl | 4-Cl | 6-CH$_3$ |
| Z1a.34 | CH$_3$ | —O— | CH$_2$C≡CH | 2-Cl | 4-Cl | 6-CH$_3$ |
| Z1a.35 | H | —S— | CH$_3$ | 2-Cl | 4-Cl | H |
| Z1a.36 | H | —S— | CH$_3$ | 2-Cl | 4-Cl | 6-Cl |
| Z1a.37 | H | —S— | CH$_2$CH$_3$ | 2-Cl | 4-Cl | H |
| Z1a.38 | H | —S— | CH$_2$CH$_3$ | 2-Cl | 4-Cl | 6-Cl |
| Z1a.39 | CH$_3$ | —S— | CH$_3$ | 2-Cl | 4-Cl | H |
| Z1a.40 | CH$_3$ | —S— | CH$_3$ | 2-Cl | 4-Cl | 6-Cl |
| Z1a.41 | CH$_3$ | —S— | CH$_2$CH$_3$ | 2-Cl | 4-Cl | H |
| Z1a.42 | CH$_3$ | —S— | CH$_2$CH$_3$ | 2-Cl | 4-Cl | 6-Cl |
| Z1a.43 | CH$_3$ | —S— | CH$_3$ | 2-Cl | 4-CF$_3$ | 6-Cl |
| Z1a.44 | CH$_3$ | —S— | CH$_3$ | 2-Cl | 4-Br | 6-Cl |
| Z1a.45 | CH$_3$ | —S— | CH$_3$ | 2-Cl | 4-C≡CH | 6-Cl |
| Z1a.46 | CH$_3$ | —S— | CH$_3$ | 2-Cl | 4-CH=NOCH$_3$ | 6-Cl |
| Z1a.47 | CH$_3$ | —S— | CH$_3$ | 2-Cl | 4-Cl | 6-CH$_3$ |
| Z1a.48 | H | —N(H)— | CH$_3$ | 2-Cl | 4-Cl | H |
| Z1a.49 | H | —N(H)— | CH$_3$ | 2-Cl | 4-Cl | 6-Cl |
| Z1a.50 | H | —N(H)— | CH$_2$CH$_3$ | 2-Cl | 4-Cl | H |
| Z1a.51 | H | —N(H)— | CH$_2$CH$_3$ | 2-Cl | 4-Cl | 6-Cl |
| Z1a.52 | CH$_3$ | —N(H)— | CH$_3$ | 2-Cl | 4-Cl | H |
| Z1a.53 | CH$_3$ | —N(H)— | CH$_3$ | 2-Cl | 4-Cl | 6-Cl |
| Z1a.54 | CH$_3$ | —N(H)— | CH$_2$CH$_3$ | 2-Cl | 4-Cl | H |
| Z1a.55 | CH$_3$ | —N(H)— | CH$_2$CH$_3$ | 2-Cl | 4-Cl | 6-Cl |
| Z1a.56 | CH$_3$ | —N(H)— | CH$_3$ | 2-Cl | 4-CF$_3$ | 6-Cl |
| Z1a.57 | CH$_3$ | —N(H)— | CH$_3$ | 2-Cl | 4-Br | 6-Cl |
| Z1a.58 | CH$_3$ | —N(H)— | CH$_3$ | 2-Cl | 4-C≡CH | 6-Cl |
| Z1a.59 | CH$_3$ | —N(H)— | CH$_3$ | 2-Cl | 4-CH=NOCH$_3$ | 6-Cl |
| Z1a.60 | CH$_3$ | —N(H)— | CH$_3$ | 2-Cl | 4-Cl | 6-CH$_3$ |
| Z1a.61 | H | —N(CH$_3$)— | CH$_3$ | 2-Cl | 4-Cl | H |
| Z1a.62 | H | —N(CH$_3$)— | CH$_3$ | 2-Cl | 4-Cl | 6-Cl |
| Z1a.63 | H | —N(CH$_3$)— | CH$_2$CH$_3$ | 2-Cl | 4-Cl | H |
| Z1a.64 | H | —N(CH$_3$)— | CH$_2$CH$_3$ | 2-Cl | 4-Cl | 6-Cl |
| Z1a.65 | CH$_3$ | —N(CH$_3$)— | CH$_3$ | 2-Cl | 4-Cl | H |

TABLE 3a-continued $$\text{(IIAa)}$$

Structure: cyclopropyl-NH-CH(R4)-CH(X-R7)-phenyl(R12, R13, R14)

| Comp. No. | R4 | X | R7 | R12 | R13 | R14 |
|---|---|---|---|---|---|---|
| Z1a.66 | CH$_3$ | —N(CH$_3$)— | CH$_3$ | 2-Cl | 4-Cl | 6-Cl |
| Z1a.67 | CH$_3$ | —N(CH$_3$)— | CH$_2$CH$_3$ | 2-Cl | 4-Cl | H |
| Z1a.68 | CH$_3$ | —N(CH$_3$)— | CH$_2$CH$_3$ | 2-Cl | 4-Cl | 6-Cl |
| Z1a.69 | CH$_3$ | —N(CH$_3$)— | CH$_3$ | 2-Cl | 4-CF$_3$ | 6-Cl |
| Z1a.70 | CH$_3$ | —N(CH$_3$)— | CH$_3$ | 2-Cl | 4-Br | 6-Cl |
| Z1a.71 | CH$_3$ | —N(CH$_3$)— | CH$_3$ | 2-Cl | 4-C≡CH | 6-Cl |
| Z1a.72 | CH$_3$ | —N(CH$_3$)— | CH$_3$ | 2-Cl | 4-CH=NOCH$_3$ | 6-Cl |
| Z1a.73 | CH$_3$ | —N(CH$_3$)— | CH$_3$ | 2-Cl | 4-Cl | 6-CH$_3$ |
| Z1a.74 | H | —N(H)O— | CH$_3$ | 2-Cl | 4-Cl | H |
| Z1a.75 | H | —N(H)O— | CH$_3$ | 2-Cl | 4-Cl | 6-Cl |
| Z1a.76 | CH$_3$ | —N(H)O— | CH$_3$ | 2-Cl | 4-Cl | H |
| Z1a.77 | CH$_3$ | —N(H)O— | CH$_3$ | 2-Cl | 4-Cl | 6-Cl |
| Z1a.78 | CH$_3$ | —N(H)O— | CH$_3$ | 2-Cl | 4-CF$_3$ | 6-Cl |
| Z1a.79 | CH$_3$ | —N(H)O— | CH$_3$ | 2-Cl | 4-Br | 6-Cl |
| Z1a.80 | CH$_3$ | —N(H)O— | CH$_3$ | 2-Cl | 4-C≡CH | 6-Cl |
| Z1a.81 | CH$_3$ | —N(H)O— | CH$_3$ | 2-Cl | 4-CH=NOCH$_3$ | 6-Cl |
| Z1a.82 | CH$_3$ | —N(H)O— | CH$_3$ | 2-Cl | 4-Cl | 6-CH$_3$ |
| Z1a.83 | H | —N(CH$_3$)O— | CH$_3$ | 2-Cl | 4-Cl | H |
| Z1a.84 | H | —N(CH$_3$)O— | CH$_3$ | 2-Cl | 4-Cl | 6-Cl |
| Z1a.85 | H | —N(CH$_3$)O— | CH$_2$CH$_3$ | 2-Cl | 4-Cl | H |
| Z1a.86 | H | —N(CH$_3$)O— | CH$_2$CH$_3$ | 2-Cl | 4-Cl | 6-Cl |
| Z1a.87 | CH$_3$ | —N(CH$_3$)O— | CH$_3$ | 2-Cl | 4-Cl | H |
| Z1a.88 | CH$_3$ | —N(CH$_3$)O— | CH$_3$ | 2-Cl | 4-Cl | 6-Cl |
| Z1a.89 | CH$_3$ | —N(CH$_3$)O— | CH$_2$CH$_3$ | 2-Cl | 4-Cl | H |
| Z1a.90 | CH$_3$ | —N(CH$_3$)O— | CH$_2$CH$_3$ | 2-Cl | 4-Cl | 6-Cl |
| Z1a.91 | CH$_3$ | —N(CH$_3$)O— | CH$_3$ | 2-Cl | 4-CF$_3$ | 6-Cl |
| Z1a.92 | CH$_3$ | —N(CH$_3$)O— | CH$_3$ | 2-Cl | 4-Br | 6-Cl |
| Z1a.93 | CH$_3$ | —N(CH$_3$)O— | CH$_3$ | 2-Cl | 4-C≡CH | 6-Cl |
| Z1a.94 | CH$_3$ | —N(CH$_3$)O— | CH$_3$ | 2-Cl | 4-CH=NOCH$_3$ | 6-Cl |
| Z1a.95 | CH$_3$ | —N(CH$_3$)O— | CH$_3$ | 2-Cl | 4-Cl | 6-CH$_3$ |
| Z1a.96 | CH3 | —O— | CH2CH3 | 2-Cl | H | H |
| Z1a.97 | CH3 | —O— | CH2CH3 | 2-Cl | 4-Cl | H |
| Z1a.98 | CH3 | —O— | CH2CH3 | 2-Cl | 4-Cl | 6-Cl |

FORMULATION EXAMPLES FOR COMPOUNDS OF FORMULA I

Example F-1.1 to F-1.3

Emulsifiable Concentrates

| Components | F-1.1 | F-1.2 | F-1.3 |
|---|---|---|---|
| comp. of Tables 1, 1a, 2 and 2a | 25% | 40% | 50% |
| calcium dodecylbenzenesulfonate | 5% | 8% | 6% |
| castor oil polyethylene glycol ether (36 mol ethylenoxy units) | 5% | — | — |
| tributylphenolpolyethylene glycol ether (30 mol ethylenoxy units) | — | 12% | 4% |
| cyclohexanone | — | 15% | 20% |
| xylene mixture | 65% | 25% | 20% |

Emulsions of any desired concentration can be prepared by diluting such concentrates with water.

Example F-2

Emulsifiable Concentrate

| Components | F-2 |
|---|---|
| comp. of Tables 1, 1a, 2 and 2a | 10% |
| octylphenolpolyethylene glycol ether (4 to 5 mol ethylenoxy units) | 3% |
| calcium dodecylbenzenesulfonate | 3% |
| castor oil polyglycol ether (36 mol ethylenoxy units) | 4% |
| cyclohexanone | 30% |
| xylene mixture | 50% |

Emulsions of any desired concentration can be prepared by diluting such concentrates with water.

Examples F-3.1 to F-3.4

Solutions

| Components | F-3.1 | F-3.2 | F-3.3 | F-3.4 |
|---|---|---|---|---|
| comp. of Tables 1, 1a, 2 and 2a | 80% | 10% | 5% | 95% |
| propylene glycol monomethyl ether | 20% | — | — | — |
| polyethylene glycol (relative molecular mass: 400 atomic mass units) | — | 70% | — | — |
| N-methylpyrrolid-2-one | — | 20% | — | — |
| epoxidised coconut oil | — | — | 1% | 5% |
| benzin (boiling range: 160-190°) | — | — | 94% | — |

The solutions are suitable for use in the form of microdrops.

Examples F-4.1 to F-4.4

Granulates

| Components | F-4.1 | F-4.2 | F-4.3 | F-4.4 |
|---|---|---|---|---|
| comp. of Tables 1, 1a, 2 and 2a | 5% | 10% | 8% | 21% |
| kaolin | 94% | — | 79% | 54% |
| highly dispersed silicic acid | 1% | — | 13% | 7% |
| attapulgite | — | 90% | — | 18% |

The novel compound is dissolved in dichloromethane, the solution is sprayed onto the carrier and the solvent is then removed by distillation under vacuum.

Examples F-5.1 and F-5.2

Dusts

| Components | F-5.1 | F-5.2 |
|---|---|---|
| comp. of Tables 1, 1a, 2 and 2a | 2% | 5% |
| highly dispersed silicic acid | 1% | 5% |
| talcum | 97% | — |
| kaolin | — | 90% |

Ready for use dusts are obtained by intimately mixing all components.

Examples F-6.1 to F-6.3

Wettable Powders

| Components | F-6.1 | F-6.2 | F-6.3 |
|---|---|---|---|
| comp. of Tables 1, 1a, 2 and 2a | 25% | 50% | 75% |
| sodium lignin sulfonate | 5% | 5% | — |
| sodium lauryl sulfate | 3% | — | 5% |
| sodium diisobutylnaphthalene sulfonate | — | 6% | 10% |
| octylphenolpolyethylene glycol ether (7 to 8 mol ethylenoxy units) | — | 2% | — |
| highly dispersed silicic acid | 5% | 10% | 10% |
| kaolin | 62% | 27% | — |

All components are mixed and the mixture is thoroughly ground in a suitable mill to give wettable powders which can be diluted with water to suspensions of any desired concentration.

Example F7

Flowable Concentrate for Seed Treatment

| | |
|---|---|
| comp. of Tables 1, 1a, 2 and 2a | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

BIOLOGICAL EXAMPLES

Fungicidal Actions

Example B-1

Action Against *Botrytis cinera* (Grey Mold) on Beans

Bean leaf disks are placed on agar in multiwell plates (24-well format) and sprayed with test solutions (0.02% active ingredient). After drying, the leaf disks are inoculated with a spore suspension of the fungus. After appropriate incubation the activity of a compound is assessed 3 days after inoculation as preventive fungicidal activity. Compounds 1.01, 1.14 and 1.15 show very good activity in this test ($\leq 20\%$ infestation). Compound 1.07 shows good activity in this test ($\leq 50\%$ infestation).

Example B-2

Action Against *Erysiphe graminis* f.sp. *tritici* (Wheat Powdery Mildew)

Wheat leaf segments are placed on agar in multiwell plates (24-well format) and sprayed with test solutions (0.02% active ingredient). After drying, the leaf disks are inoculated with a spore suspension of the fungus. After appropriate incubation the activity of a compound is assessed 7 days after inoculation as preventive fungicidal activity. Compounds 1.14 and 1.15 show very good activity in this test (≦20% infestation). Compound 1.01 shows good activity in this test (≦50% infestation).

Example B-3

Action Against *Pyrenophora teres* (Net Blotch) on Barley

Barley leaf segments are placed on agar in multiwell plates (24-well format) and sprayed with test solutions (0.02% active ingredient). After drying, the leaf disks are inoculated with a spore suspension of the fungus. After appropriate incubation the activity of a compound is assessed 4 days after inoculation as preventive fungicidal activity. Compounds 1.01, 1.07, 1.14, 1.15 and 1.76 show very good activity in this test (≦20% infestation).

Example B-4

Action Against *Mycosphaerella arachidis* (Early Leaf Spot of Groundnut; *Cercospora arachidicola* [anamorph])—Fungal Growth Assay Conidia of the fungus from cryogenic storage are directly mixed into nutrient broth (PDB potato dextrose broth). After placing a (DMSO) solution of the test compounds (0.002% active ingredient) into a microtiter plate (96-well format) the nutrient broth containing the fungal spores is added. The test plates are incubated at 24° C. and the inhibition of growth is measured photometrically after 6-7 days. The activity of a compound is expressed as fungal growth inhibition (0=no growth inhibition, ratings of 80% to 99% mean good to very good inhibition, 100%=complete inhibition). Compounds 1.01, 1.14 and 1.15 show very good activity in this test (≦80% inhibition). Compounds 1.07 and 2.01 show good activity in this test (≦50% inhibition).

Example B-5

Action Against *Septoria tritici*—Fungal Growth Assay

Conidia of the fungus from cryogenic storage are directly mixed into nutrient broth (PDB potato dextrose broth). After placing a (DMSO) solution of the test compounds (0.002% active ingredient) into a microtiter plate (96-well format) the nutrient broth containing the fungal spores is added. The test plates are incubated at 24° C. and the inhibition of growth is determined photometrically after 72 hrs. The activity of a compound is expressed as fungal growth inhibition (0=no growth inhibition, ratings of 80% to 99% mean good to very good inhibition, 100%=complete inhibition). Compounds 1.01, 1.07, 1.14, 1.15, 1.76 and 2.01 show very good activity in this test (≦80% inhibition).

Example B-6

Action Against *Monographella nivalis* (Anamorph: *Fusarium nivale, Microdochium nivale*; Snow Mould)—Fungal Growth Assay Conidia of the fungus from cryogenic storage are directly mixed into nutrient broth (PDB potato dextrose broth). After placing a DMSO-solution of the test compounds (0.002% active ingredient) into a microtiter plate (96-well format) the nutrient broth containing the fungal spores is added. The test plates are incubated at 24° C. and the inhibition of growth is measured photometrically after 72 hrs (0=no growth inhibition, ratings of 80% to 99% mean good to very good inhibition, 100%=complete inhibition). Compounds 1.14 and 1.15 show very good activity in this test (≦80% inhibition).

Example B-7

Action Against *Pseudocercosporella herpotrichoides* var. *acuformis* (Eyespot/Cereals)—Fungal Growth Assay Conidia of the fungus from cryogenic storage are directly mixed into nutrient broth (PDB potato dextrose broth). After placing a (DMSO) solution of the test compounds (0.002% active ingredient) into a microtiter plate (96-well format) the nutrient broth containing the fungal spores is added. The test plates are incubated at 24° C. and the inhibition of growth is determined photometrically after 72 hrs. The activity of a compound is expressed as fungal growth inhibition (0=no growth inhibition, ratings of 80% to 99% mean good to very good inhibition, 100%=complete inhibition). Compounds 1.01, 1.14 and 1.15 show very good activity in this test (≦30% inhibition).

What is claimed is:
1. A compound of the formula I

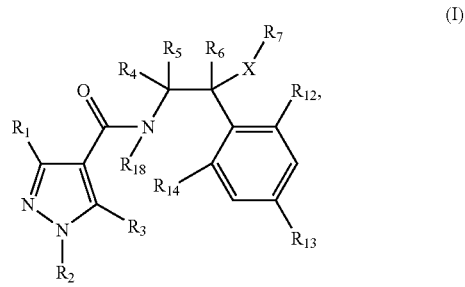

wherein
$R_1$ is halogenmethyl;
$R_2$ is $C_1$-$C_4$alkyl, $C_1$-$C_4$halogenalkyl, $C_1$-$C_4$alkoxy-$C_1$-$C_4$alkyl or $C_1$-$C_4$halogenalkoxy-$C_1$-$C_4$alkyl; and
$R_3$ is hydrogen, halogen or cyano;
$R_4$, $R_5$ and $R_6$ independently of each other stand for hydrogen, halogen, nitro, $C_1$-$C_6$alkyl, which is unsubstituted or substituted by one or more substituents $R_8$, $C_3$-$C_6$cycloalkyl, which is unsubstituted or substituted by one or more substituents $R_8$, $C_2$-$C_6$alkenyl, which is unsubstituted or substituted by one or more substituents $R_8$, $C_2$-$C_6$alkynyl, which is unsubstituted or substituted by one or more substituents $R_8$;
or $R_4$ and $R_5$ together are a $C_2$-$C_5$alkylene group, which is unsubstituted or substituted by one or more $C_1$-$C_6$alkyl groups;
X is oxygen, sulfur, —N($R_{10}$)— or —N($R_{11}$)—O—;
$R_{10}$ and $R_{11}$ independently of each other stands for hydrogen or $C_1$-$C_6$alkyl;
$R_7$ stands for $C_1$-$C_6$alkyl, which is unsubstituted or substituted by one or more substituents $R_9$, $C_3$-$C_6$cycloalkyl, which is unsubstituted or substituted by one or more substituents $R_9$, $C_2$-$C_6$alkenyl, which is unsubstituted or substituted by one or more substituents $R_9$, $C_2$-$C_6$alkynyl, which is unsubstituted or substituted by one or more substituents $R_9$;

$R_{12}$ stands for halogen, $C_1$-$C_6$haloalkoxy, $C_1$-$C_6$haloalkylthio, cyano, nitro, —C($R^a$)=N(O$R^b$), $C_1$-$C_6$alkyl, which is unsubstituted or substituted by one or more 2 of 6 substituents $R_{15}$, $C_3$-$C_6$cycloalkyl, which is unsubstituted or substituted by one or more substituents $R_{15}$, $C_6$-$C_{14}$bicycloalkyl, which is unsubstituted or substituted by one or more substituents $R_{15}$, $C_2$-$C_6$alkenyl, which is unsubstituted or substituted by one or more substituents $R_{15}$, $C_2$-$C_6$alkynyl, which is unsubstituted or substituted by one or more substituents $R_{15}$, phenyl, which is unsubstituted or substituted by one or more substituents $R_{15}$, phenoxy, which is unsubstituted or substituted by one or more substituents $R_{15}$ or pyridinyloxy, which is unsubstituted or substituted by one or more substituents $R_{15}$;

$R_{13}$ stands for hydrogen, halogen, $C_1$-$C_6$haloalkoxy, $C_1$-$C_6$haloalkylthio, cyano, nitro, —C($R^c$)=N(O$R^d$), $C_1$-$C_6$alkyl, which is unsubstituted or substituted by one or more substituents $R_{16}$, $C_3$-$C_6$cycloalkyl, which is unsubstituted or substituted by one or more substituents $R_{16}$, $C_6$-$C_{14}$bicycloalkyl, which is unsubstituted or substituted by one or more substituents $R_{16}$, $C_2$-$C_6$alkenyl, which is unsubstituted or substituted by one or more substituents $R_{16}$, $C_2$-$C_6$alkynyl, which is unsubstituted or substituted by one or more substituents $R_{16}$, phenyl, which is unsubstituted or substituted by one or more substituents $R_{16}$, phenoxy, which is unsubstituted or substituted by one or more substituents $R_{16}$ or pyridinyloxy, which is unsubstituted or substituted by one or more substituents $R_{16}$;

$R_{14}$ stands for hydrogen, halogen, $C_1$-$C_6$haloalkoxy, $C_1$-$C_6$haloalkylthio, cyano, nitro, —C($R^e$)=N(O$R^f$), $C_1$-$C_6$alkyl, which is unsubstituted or substituted by one or more substituents $R_{17}$, $C_3$-$C_6$cycloalkyl, which is unsubstituted or substituted by one or more substituents $R_{17}$, $C_6$-$C_{14}$bicycloalkyl, which is unsubstituted or substituted by one or more substituents $R_{17}$, $C_2$-$C_6$alkenyl, which is unsubstituted or substituted by one or more substituents $R_{17}$, $C_2$-$C_6$alkynyl, which is unsubstituted or substituted by one or more substituents $R_{17}$, phenyl, which is unsubstituted or substituted by one or more substituents $R_{17}$, phenoxy, which is unsubstituted or substituted by one or more substituents $R_{17}$ or pyridinyloxy, which is unsubstituted or substituted by one or more substituents $R_{17}$;

each $R_8$, $R_9$, $R_{15}$, $R_{16}$ and $R_{17}$ is independently of each other halogen, nitro, $C_1$-$C_6$alkoxy, $C_1$-$C_6$halogenalkoxy, $C_1$-$C_6$alkylthio, $C_1$-$C_6$halogenalkylthio, $C_3$-$C_6$alkenyloxy, $C_3$-$C_6$alkynyloxy or —C($R^g$)=N(O$R^h$);

each $R^a$, $R^c R^e$ and $R^g$ is independently of each other hydrogen or $C_1$-$C_6$alkyl;

each $R^b$, $R^d R^f$ and $R^h$ is independently of each other $C_1$-$C_6$alkyl;

$R_{18}$ is hydrogen or $C_3$-$C_7$cycloalkyl;

and tautomers/stereoisomers/enantiomers of these compounds.

2. A compound of formula I according to claim 1, wherein $R_{18}$ is hydrogen.

3. A compound of formula I according to claim 1, wherein $R_1$ is $CF_3$, $CF_2H$ or $CFH_2$; $R_2$ is $C_1$-$C_4$alkyl; and $R_3$ is hydrogen or halogen.

4. A compound of formula I according to claim 1, wherein $R_1$ is $CF_2H$; $R_2$ is methyl and $R_3$ is hydrogen.

5. A compound of formula I according to claim 1, wherein $R_4$ is hydrogen or $C_1$-$C_6$alkyl, which is unsubstituted or substituted by one or more substituents $R_8$.

6. A compound of formula I according to claim 1, wherein $R_4$ is hydrogen or methyl.

7. A compound of formula I according to claim 1, wherein $R_4$ is methyl.

8. A compound of formula I according to claim 1, wherein $R_5$ and $R_6$ both are hydrogen.

9. A compound of formula I according to claim 1, wherein X is oxygen.

10. A compound of formula I according to claim 9, wherein $R_7$ stands for $C_1$-$C_6$alkyl, which is unsubstituted or substituted by one or more substituents $R_9$, $C_2$-$C_6$alkenyl, which is unsubstituted or substituted by one or more substituents $R_9$ or $C_2$-$C_6$alkynyl, which is unsubstituted or substituted by one or more substituents $R_9$.

11. A compound of formula I according to claim 10, wherein $R_7$ is methyl.

12. A compound of formula I according to claim 1, wherein X is —N($R_{10}$)— or —N($R_{11}$)—O—.

13. A method of controlling or preventing infestation of useful plants by phytopathogenic microorganisms, wherein a compound of formula I according to claim 1 or a composition, comprising this compound as active ingredient, is applied to the plants, to parts thereof or the locus thereof.

14. A composition for controlling and protecting against phytopathogenic microorganisms, comprising a compound of formula I according to claim 1 and an inert carrier.

* * * * *